(12) United States Patent
Calvert et al.

(10) Patent No.: US 6,979,829 B2
(45) Date of Patent: Dec. 27, 2005

(54) DEVICES AND METHODS FOR DETERMINING THE AMOUNT OF ENERGY ABSORBED DURING IRRADIATION

(75) Inventors: Glenn Calvert, Frederick, MD (US); David Clark, Shawnee, CO (US); Martin J. MacPhee, North Potomac, MD (US); Randall Kent, Thousand Oaks, CA (US); Anna L. McBain, Derwood, MD (US); Bryant O. Pearce, North East, MD (US)

(73) Assignee: Clearant Inc., Los Angeles, CA (US)

( * ) Notice: Subject to any disclaimer, the term of this patent is extended or adjusted under 35 U.S.C. 154(b) by 0 days.

(21) Appl. No.: 10/420,932

(22) Filed: Apr. 23, 2003

(65) Prior Publication Data

US 2004/0211916 A1    Oct. 28, 2004

(51) Int. Cl.[7] .................................. G01T 1/02
(52) U.S. Cl. .................................. 250/472.1
(58) Field of Search ............... 250/472.1, 473.1, 250/474.1; 422/22, 25

(56) References Cited

U.S. PATENT DOCUMENTS

| | | | |
|---|---|---|---|
| 4,668,714 A | 5/1987 | Morita et al. | 523/136 |
| 5,066,863 A | 11/1991 | Hanisch et al. | 250/474.1 |
| 5,151,486 A | 9/1992 | Washio et al. | 528/124 |
| 6,157,028 A | 12/2000 | Purtle | 250/252.1 |
| 6,187,572 B1 * | 2/2001 | Platz et al. | 435/173.3 |
| 6,232,365 B1 * | 5/2001 | Weiss et al. | 522/178 |
| 6,249,004 B1 | 6/2001 | Miller | 250/474.1 |
| 6,376,845 B1 | 4/2002 | Purtle | 250/491.1 |
| 6,384,419 B1 | 5/2002 | Purtle | 250/526 |
| 6,531,217 B1 | 3/2003 | Martin et al. | 428/364 |

OTHER PUBLICATIONS

A.S. Meyer, Jr. and C. M. Boyd, "Determination of Water by Titration with Coulometrically Generated Karl Fischer Reagent," Analytical Chemistry, vol. 31, No. 2, Feb. 1959, pp. 215-219.

Center for Biologics Evaluation and Research, "Guideline for the Determination of Residual Moisture in Dried Biological Products," FDA, Jan. 1990, pp. 83-93.

* cited by examiner

Primary Examiner—Constantine Hannaher
(74) Attorney, Agent, or Firm—Morgan, Lewis & Bockius LLP

(57) ABSTRACT

Devices and methods are disclosed for determining the amount of energy absorbed during irradiation. Such devices comprise a material that absorbs radiation in a quantifiable manner and a cooling agent to maintain the temperature of that material within a predetermined range, and may be used to determine the amount of energy absorbed during irradiation, for example during sterilization of a biological material.

45 Claims, 10 Drawing Sheets y = dosimeter t = thermal label

DEVICES AND METHODS FOR DETERMINING THE AMOUNT OF ENERGY ABSORBED DURING IRRADIATION

BACKGROUND OF THE INVENTION

1. Field of the Invention

The present invention relates to devices and methods for determining the amount of energy absorbed during irradiation. The present invention particularly relates to devices comprising a material that absorbs radiation in a quantifiable manner and a cooling agent to maintain the temperature of that material within a predetermined range, and the use of these devices for determining the amount of energy absorbed during irradiation, for example during sterilization of a biological material.

2. Background of the Related Art

Many biological materials that are prepared for human, veterinary, diagnostic and/or experimental use may contain unwanted and potentially dangerous biological contaminants or pathogens, such as viruses, bacteria, in both vegetative and spore states, yeasts, molds, fungi, prions or similar agents responsible, alone or in combination, for TSEs and/or single-cell or multicellular parasites. Consequently, it is of utmost importance that any biological contaminant or pathogen in the biological material be inactivated before the product is used. This is especially critical when the material is to be administered directly to a patient, for example in blood transfusions, blood factor replacement therapy, tissue implants, including organ transplants, and other forms of human and/or other animal therapy corrected or treated by surgical implantation, intravenous, intramuscular or other forms of injection or introduction. This is also critical for the various biological materials that are prepared in media or via the culture of cells, or recombinant cells which contain various types of plasma and/or plasma derivatives or other biologic materials and which may be subject to mycoplasmal, prion, ureaplasmal, bacterial, viral and/or other biological contaminants or pathogens.

In order to inactivate such biological contaminants or pathogens, it is often desirable to expose the biological material to radiation. For instance, viruses and bacteria are readily inactivated by gamma radiation at high total doses.

In order to determine the amount of radiation received by a biological material during treatment with radiation, dosimetry is employed. Dosimetry is the part of a radiation process where the amount of energy absorbed during irradiation is quantified. Dosimetry is employed, for instance, to correctly monitor radiation processes during the development, validation and routine process control stages.

For instance, when irradiating biological materials to inactivate biological contaminants and pathogens, dosimetry may be used to determine whether the amount of radiation received by the biological product during irradiation is within a predetermined range. If the amount of radiation received is below a predetermined amount, the contaminants or pathogens in the biological material may not be inactivated. Conversely, if the amount of radiation received is above a predetermined amount, the biological material may lose biological activity. In either case, the biological material would be unsuitable for use.

Dosimeters are devices that, when irradiated, exhibit a quantifiable and reproducible change in some property of the device that may be related to absorbed dose in a given material. Physical and/or chemical changes take place in the device than can be measured using appropriate analytical instrumentation and techniques.

Examples of solid state dosimeters include thermoluminescent dosimeters, lyoluminescent dosimeters, polymethyl methacrylate dosimeters, radiochromicatic film dosimeters, cobalt glass dosimeters and alanine dosimeters. Dosimeters may have various geometries, such as pellets, films and cylinders.

In practice, the dosimeter is irradiated and the amount of radiation received is determined by measuring a characteristic of the dosimeter sensitive to the radiation. For instance, depending on the type of dosimeter employed, luminescence, absorption, or free radical generation may be measured.

When the crystalline form of alanine is irradiated, stable, characteristic free radicals are produced. The number of free radicals is proportional to the radiation dose absorbed by the crystal. By determining the amount of free radicals produced during irradiation, the dose of radiation received may be determined. For alanine dosimeters, the amount of free radicals produced is typically determined by electron spin resonance spectroscopy (ESR). The free radicals generated during irradiation of alanine remain stable; their concentration is subject to only a minor amount of time-dependent change. Additionally, the free radicals generated in crystalline alanine are relatively stable with respect to heat. Examples of alanine dosimeters are disclosed in U.S. Pat. Nos. 4,668,714 and 5,066,863.

Dosimeters may also be used for dose mapping. The process of dose mapping typically includes simulating radiation conditions to be employed for a sample of interest. A dosimeter is fixed in, on or near a simulated sample, the simulated sample is irradiated and the amount of radiation received by the dosimeter during irradiation is determined. The amount of radiation received by the dosimeter corresponds to the amount received by the simulated sample.

U.S. Pat. No. 6,157,028 to Purtle discloses a method of dose mapping. According to Purtle, a dosimeter is packed inside a container under conditions that simulate the conditions under which a material of interest is to be irradiated, e.g., the density of the material within the container approximates the density of the material to be irradiated, the relationship between the container and the radiation source approximates that to be used during irradiation of the material of interest, etc. A mixture of dry animal food and salt pellets approximating the density of dry ice is packed around the container and the container is irradiated. Following irradiation, the dosimeter is analyzed.

Purtle teaches that biological materials are typically irradiated at temperatures below ambient, but states that a dry ice substitute is employed during dose mapping because "[d]osimeters . . . do not give accurate data in cold conditions . . . " In addition to the dry ice substitute, a material other than the material of interest is employed, such as agar.

The above references are incorporated by reference herein where appropriate for teachings of additional or alternative details, features and/or technical background.

SUMMARY OF THE INVENTION

An object of the invention is to solve at least the related art problems and disadvantages, and to provide at least the advantages described hereinafter.

Accordingly, it is an object of the present invention to provide methods for determining the amount of energy absorbed by a product undergoing sterilization with radiation.

Accordingly, it is another object of the present invention to provide devices for measuring the amount of energy absorbed by a product undergoing irradiation.

Another object of the present invention is to provide a method for maintaining the temperature of a product undergoing irradiation within a predetermined temperature range.

In accordance with these and other objectives, a first embodiment of the present invention is directed to a device for measuring the amount of energy absorbed by a product undergoing irradiation, comprising: (i) an effective amount of at least one material that absorbs radiation in a quantifiable manner; and (ii) an effective amount of at least one cooling agent for maintaining the material within a predetermined temperature range between −120° C. and ambient temperature during irradiation.

A second embodiment of the present invention is directed to a method for determining the amount of energy absorbed by a product undergoing irradiation, comprising: (a) placing within a suitable container at least one product to be irradiated and at least one device comprising: (i) at least one material that absorbs radiation in a quantifiable manner; and (ii) an effective amount of at least one cooling agent for maintaining the material within a predetermined temperature range between −120° C. and ambient temperature during irradiation; (b) irradiating the container containing the product and the device; and (c) analyzing the material to determine the amount of energy absorbed during irradiation.

A third embodiment of the present invention is directed to a method for maintaining the temperature of a product undergoing irradiation within a predetermined temperature range between −120° C. and ambient temperature, comprising: (a) placing at least one product to be irradiated in a suitable container having at least one side and a bottom, wherein the volume defined by said container is greater than the volume of the product; (b) placing an effective amount of at least one cooling agent in the container between the product and the at least one side; and (c) irradiating the container containing the product and the cooling agent with ionizing radiation.

Other objects, features and advantages of the present invention will be set forth in the detailed description of preferred embodiments that follows, and in part will be apparent from the description or may be learned by practice of the invention. These objects and advantages of the invention will be realized and attained by the compositions and methods particularly pointed out in the written description and claims hereof.

DETAILED DESCRIPTION OF PREFERRED EMBODIMENTS

A. Definitions

Figure 1:
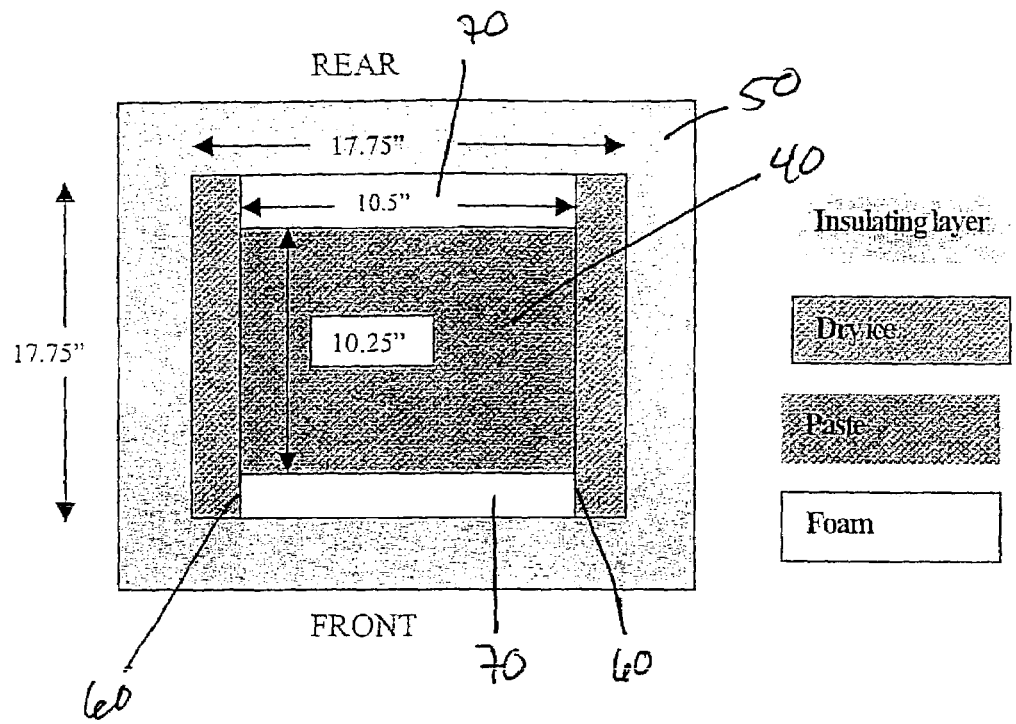
FIG. 1 shows a device according to a preferred embodiment of the present invention.

Unless defined otherwise, all technical and scientific terms used herein are intended to have the same meaning as is commonly understood by one of ordinary skill in the relevant art.

As used herein, the singular forms "a," "an," and "the" include the plural reference unless the context clearly dictates otherwise.

As used herein, the term "biological material" is intended to mean any substance derived or obtained from a living organism. Illustrative examples of biological materials include, but are not limited to, the following: cells; tissues; blood or blood components; proteins, including recombinant and transgenic proteins, and proteinaceous materials; enzymes, including digestive enzymes, such as trypsin, chymotrypsin, alpha-glucosidase and iduronodate-2-sulfatase; immunoglobulins, including mono and polyimmunoglobulins; botanicals; food; and the like. Preferred examples of biological materials include, but are not limited to, the following: ligaments; tendons; nerves; bone, including demineralized bone matrix, grafts, joints, femurs, femoral heads, etc.; teeth; skin grafts; bone marrow, including bone marrow cell suspensions, whole or processed; heart valves; cartilage; corneas; arteries and veins; organs, including organs for transplantation, such as hearts, livers, lungs, kidneys, intestines, pancreas, limbs and digits; lipids; carbohydrates; collagen, including native, afibrillar, atelomeric, soluble and insoluble, recombinant and transgenic, both native sequence and modified; enzymes; chitin and its derivatives, including NO-carboxy chitosan (NOCC); stem cells, islet of Langerhans cells and other cells for transplantation, including genetically altered cells; red blood cells; white blood cells, including monocytes; and platelets.

As used herein, the term "sterilize" is intended to mean a reduction in the level of at least one active biological contaminant or pathogen found in the preparation containing a biological material being treated according to the present invention.

As used herein, the term "non-aqueous solvent" is intended to mean any liquid other than water in which a biological material may be dissolved or suspended or which may be disposed within a biological material and includes both inorganic solvents and, more preferably, organic solvents. Illustrative examples of suitable non-aqueous solvents include, but are not limited to, the following: alkanes and cycloalkanes, such as pentane, 2-methylbutane (isopentane), heptane, hexane, cyclopentane and cyclohexane; alcohols, such as methanol, ethanol, 2-methoxyethanol, isopropanol, n-butanol, t-butyl alcohol, and octanol; esters, such as ethyl acetate, 2-methoxyethyl acetate, butyl acetate and benzyl benzoate; aromatics, such as benzene, toluene, pyridine, xylene; ethers, such as diethyl ether, 2-ethoxyethyl ether, ethylene glycol dimethyl ether and methyl t-butyl ether; aldehydes, such as formaldehyde and glutaraldehyde; ketones, such as acetone and 3-pentanone (diethyl ketone); glycols, including both monomeric glycols, such as ethylene glycol and propylene glycol, and polymeric glycols, such as polyethylene glycol (PEG) and polypropylene glycol (PPG), e.g., PPG 400, PPG 1200 and PPG 2000; acids and acid anhydrides, such as formic acid, acetic acid, trifluoroacetic acid, phosphoric acid and acetic anhydride; oils, such as cottonseed oil, peanut oil, culture media, polyethylene glycol, poppyseed oil, safflower oil, sesame oil, soybean oil and vegetable oil; amines and amides, such as piperidine, N,N-dimethylacetamide and N,N-dimethylformamide; dimethylsulfoxide (DMSO); nitriles, such as benzonitrile and acetonitrile; hydrazine; detergents, such as polyoxyethylenesorbitan monolaurate (Tween 20) and monooleate (Tween 80), Triton and sodium dodecyl sulfate; carbon disulfide; halogenated solvents, such as dichloromethane, chloroform, carbon tetrachloride, 1,2-dichlorobenzene, 1,2-dichloroethane, tetrachloroethylene and 1-chlorobutane; furans, such as tetrahydrofuran; oxanes, such as 1,4-dioxane; and glycerin/glycerol. Particularly preferred examples of suitable non-aqueous solvents include non-aqueous solvents which also function as stabilizers, such as ethanol and acetone.

As used herein, the term "biological contaminant or pathogen" is intended to mean a biological contaminant or pathogen that, upon direct or indirect contact with a biological material may have a deleterious effect on the biological material or upon a recipient thereof. Such biological contaminants or pathogens include the various viruses, bacteria, in both vegetative and spore states (including inter- and intracellular bacteria, such as mycoplasmas, ureaplasmas, nanobacteria, chlamydia, rickettsias), yeasts, molds, fungi, prions or similar agents responsible, alone or in combination, for TSEs and/or single or multicellular parasites known to those of skill in the art to generally be found in or infect biological materials. Examples of other biological contaminants or pathogens include, but are not limited to, the following: viruses, such as human immunodeficiency viruses and other retroviruses, herpes viruses, filoviruses, circoviruses, paramyxoviruses, cytomegaloviruses, hepatitis viruses (including hepatitis A, B, C, and D variants thereof, among others), pox viruses, toga viruses, Ebstein-Barr viruses and parvoviruses; bacteria, such as *Escherichia, Bacillus, Campylobacter, Streptococcus* and *Staphylococcus*; nanobacteria; parasites, such as *Trypanosoma* and malarial parasites, including *Plasmodium* species; yeasts; molds; fungi; mycoplasmas and ureaplasmas; chlamydia; rickettsias, such as *Coxiella* bumetti; and prions and similar agents responsible, alone or in combination, for one or more of the disease states known as transmissible spongiform encephalopathies (TSEs) in mammals, such as scrapie, transmissible mink encephalopathy, chronic wasting disease (generally observed in mule deer and elk), feline spongiform encephalopathy, bovine spongiform encephalopathy (mad cow disease), Creutzfeld-Jakob disease (including variant CJD), Fatal Familial Insomnia, Gerstmann-Straeussler-Scheinker syndrome, kuru and Alpers syndrome. As used herein, the term "active biological contaminant or pathogen" is intended to mean a biological contaminant or pathogen that is capable of causing a deleterious effect, either alone or in combination with another factor, such as a second biological contaminant or pathogen or a native protein (wild-type or mutant) or antibody, in a biological material and/or a recipient thereof.

As used herein, the term "a biologically compatible solution" is intended to mean a solution to which a biological material may be exposed, such as by being suspended or dissolved therein, and retain its essential biological and physiological characteristics. Such solutions may be of any suitable pH, tonicity, concentration and/or ionic strength.

As used herein, the term "a biologically compatible buffered solution" is intended to mean a biologically compatible solution having a pH and osmotic properties (e.g., tonicity, osmolality and/or oncotic pressure) suitable for maintaining the integrity of the material(s) therein. Suitable biologically compatible buffered solutions typically have a pH between 2 and 8.5 and are isotonic or only moderately hypotonic or hypertonic. Biologically compatible buffered solutions are known and readily available to those of skill in the art. Greater or lesser pH and/or tonicity may also be used in certain applications. The ionic strength of the solution may be high or low, but is typically similar to the environments in which the tissue is intended to be used.

As used herein, the term "stabilizer" is intended to mean a compound or material that, alone and/or in combination, reduces damage to the biological material being irradiated to a level that is insufficient to preclude the safe and effective use of the material. Illustrative examples of stabilizers that are suitable for use include, but are not limited to, the following, including structural analogs and derivatives thereof: antioxidants; free radical scavengers, including spin traps, such as tert-butyl-nitrosobutane (tNB), α-phenyl-tert-butylnitrone (PBN), 5,5-dimethylpyrroline-N-oxide (DMPO), tert-butylnitrosobenzene (BNB), α-(4-pyridyl-1-oxide)-N-tert-butylnitrone (4-POBN) and 3,5-dibromo-4-nitroso-benzenesulphonic acid (DBNBS); combination stabilizers, i.e., stabilizers which are effective at quenching both Type I and Type II photodynamic reactions; and ligands, ligand analogs, substrates, substrate analogs, modulators, modulator analogs, stereoisomers, inhibitors, and inhibitor analogs, such as heparin, that stabilize the molecule(s) to which they bind. Preferred examples of additional stabilizers include, but are not limited to, the following: fatty acids, including 6,8-dimercapto-octanoic acid (lipoic acid) and its derivatives and analogues (alpha, beta, dihydro, bisnor and tetranor lipoic acid), thioctic acid, 6,8-dimercapto-octanoic acid, dihydrolopoate (DL-6,8-dithioloctanoic acid methyl ester), lipoamide, bisonor methyl ester and tetranor-dihydrolipoic acid, omega-3 fatty acids, omega-6 fatty acids, omega-9 fatty acids, furan fatty acids, oleic, linoleic, linolenic, arachidonic, eicosapentaenoic (EPA), docosahexaenoic (DHA), and palmitic acids and their salts and derivatives; carotenes, including alpha-, beta-, and gamma-carotenes; Co-Q10; xanthophylls; sucrose, polyhydric alcohols, such as glycerol, mannitol, inositol, and sorbitol; sugars, including derivatives and stereoisomers thereof, such as xylose, glucose, ribose, mannose, fructose, erythrose, threose, idose, arabinose, lyxose, galactose, allose, altrose, gulose, talose, and trehalose; amino acids and derivatives thereof, including both D- and L-forms and mixtures thereof, such as arginine, lysine, alanine, valine, leucine, isoleucine, proline, phenylalanine, glycine, serine, threonine, tyrosine, asparagine, glutamine, aspartic acid, histidine, N-acetylcysteine (NAC), glutamic acid, tryptophan, sodium capryl N-acetyl tryptophan, and methionine; azides, such as sodium azide; enzymes, such as Superoxide Dismutase (SOD), Catalase, and Δ4, Δ5 and Δ6 desaturases; uric acid and its derivatives, such as 1,3-dimethyluric acid and dimethylthiourea; allopurinol; thiols, such as glutathione and reduced glutathione and cysteine; trace elements, such as selenium, chromium, and boron; vitamins, including their precursors and derivatives, such as vitamin A, vitamin C (including its derivatives and salts such as sodium ascorbate and palmitoyl ascorbic acid) and vitamin E (and its derivatives and salts such as alpha-, beta-, gamma-, delta-, epsilon-, zeta-, and eta-tocopherols, tocopherol acetate and alpha-tocotrienol); chromanol-alpha-C6; 6-hydroxy-2,5,7,8-tetramethylchroma-2 carboxylic acid (Trolox) and derivatives; extraneous proteins, such as gelatin and albumin; tris-3-methyl-1-phenyl-2-pyrazolin-5-one (MCI-186); citiolone; puercetin; chrysin; dimethyl sulfoxide (DMSO); piperazine diethanesulfonic acid (PIPES); imidazole; methoxypsoralen (MOPS); 1,2-dithiane-4, 5-diol; reducing substances, such as butylated hydroxyanisole (BHA) and butylated hydroxytoluene (BHT); cholesterol, including derivatives and its various oxidized and reduced forms thereof, such as low density lipoprotein (LDL), high density lipoprotein (HDL), and very low density lipoprotein (VLDL); probucol; indole derivatives; thimerosal; lazaroid and tirilazad mesylate; proanthenols; proanthocyanidins; ammonium sulfate; Pegorgotein (PEG-SOD); N-tert-butyl-alpha-phenylnitrone (PBN); 4-hydroxy-2,2,6,6-tetramethylpiperidin-1-oxyl (Tempol); mixtures of ascorbate, urate and Trolox C (Asc/urate/Trolox C); proteins, such as albumin, and peptides of two or more amino acids, any of which may be either naturally occurring amino acids, i.e., L-amino acids, or non-naturally occurring amino acids, i.e., D-amino acids, and mixtures, derivatives, and analogs thereof, including, but not limited to, arginine, lysine, alanine, valine, leucine, isoleucine, proline, phenylalanine, glycine, histidine, glutamic acid, tryptophan (Trp), serine, threonine, tyrosine, asparagine, glutamine, aspartic acid, cysteine, methionine, and derivatives thereof, such as N-acetylcysteine (NAC) and sodium capryl N-acetyl tryptophan, as well as homologous dipeptide stabilizers (composed of two identical amino acids), including such naturally occurring amino acids, as Gly-Gly (glycylglycine) and Trp-Trp, and heterologous dipeptide stabilizers (composed of different amino acids), such as carnosine (β-alanyl-histidine), anserine (β-alanyl-methylhistidine), and Gly-Trp; and flavonoids/flavonols, such as diosmin, quercetin, rutin, silybin, silidianin, silicristin, silymarin, apigenin, apiin, chrysin, morin, isoflavone, flavoxate, gossypetin, myricetin, biacalein, kaempferol, curcumin, proanthocyanidin B2-3-O-gallate, epicatechin gallate, epigallocatechin gallate, epigallocatechin, gallic acid, epicatechin, dihydroquercetin, quercetin chalcone, 4,4'-dihydroxy-chalcone, isoliquiritigenin, phloretin, coumestrol, 4', 7-dihydroxy-flavanone, 4', 5-dihydroxyflavone, 4', 6-dihydroxy-flavone, luteolin, galangin, equol, biochanin A, daidzein, formononetin, genistein, amentoflavone, bilobetin, taxifolin, delphinidin, malvidin, petunidin, pelargonidin, malonylapiin, pinosylvin, 3-methoxyapigenin, leucodelphinidin, dihydrokaempferol, apigenin 7-O-glucoside, pycnogenol, aminoflavone, purpurogallin fisetin, 2', 3'-dihydroxyflavone, 3-hydroxyflavone, 3', 4'-dihydroxyflavone, catechin, 7-flavonoxyacetic acid ethyl ester, catechin, hesperidin, and naringin. Particularly preferred examples include single stabilizers or combinations of stabilizers that are effective at quenching both Type I and Type II photodynamic reactions, and volatile stabilizers, which can be applied as a gas and/or easily removed by evaporation, low pressure, and similar methods. Additional preferred examples for use in the methods of the present invention include hydrophobic stabilizers.

As used herein, the term "residual solvent content" is intended to mean the amount or proportion of freely-available liquid in the biological material. Freely-available liquid means the liquid, such as water and/or an organic solvent (e.g., ethanol, isopropanol, polyethylene glycol, etc.), present in the biological material being sterilized that is not bound to or complexed with one or more of the non-liquid components of the biological material. Freely-available liquid includes intracellular water and/or other solvents. The residual solvent contents related as water referenced herein refer to levels determined by the FDA approved, modified Karl Fischer method (Meyer and Boyd, Analytical Chem., 31:215–219, 1959; May, et al., J. Biol. Standardization, 10:249–259, 1982; Centers for Biologics Evaluation and Research, FDA, Docket No. 89D-0140, 83–93; 1990) or by near infrared spectroscopy. Quantitation of the residual levels of water or other solvents may be determined by means well known in the art, depending upon which solvent is employed. The proportion of residual solvent to solute may also be considered to be a reflection of the concentration of the solute within the solvent. When so expressed, the greater the concentration of the solute, the lower the amount of residual solvent.

As used herein, the term "sensitizer" is intended to mean a substance that selectively targets viruses, bacteria, in both vegetative and spore states (including inter- and intracellular bacteria, such as mycoplasmas, ureaplasmas, nanobacteria, chlamydia, rickettsias), yeasts, molds, fungi, single or multicellular parasites, and/or prions or similar agents responsible, alone or in combination, for TSEs, rendering them more sensitive to inactivation by radiation, therefore permitting the use of a lower rate or dose of radiation and/or a shorter time of irradiation than in the absence of the sensitizer. Illustrative examples of suitable sensitizers include, but are not limited to, the following: psoralen and its derivatives and analogs (including 3-carboethoxy psoralens); inactines and their derivatives and analogs; angelicins, khellins and coumarins which contain a halogen substituent and a water solubilization moiety, such as quaternary ammoniumion or phosphonium ion; nucleic acid binding compounds; brominated hematoporphyrin; phthalocyanines; purpurins; porphyrins; halogenated or metal atom-substituted derivatives of dihematoporphyrin esters, hematoporphyrin derivatives, benzoporphyrin derivatives, hydrodibenzoporphyrin dimaleimade, hydrodibenzoporphyrin, dicyano disulfone, tetracarbethoxy hydrodibenzoporphyrin, and tetracarbethoxy hydrodibenzoporphyrin dipropionamide; doxorubicin and daunomycin, which may be modified with halogens or metal atoms; netropsin; BD peptide, S2 peptide; S-303 (ALE compound); dyes, such as hypericin, methylene blue, eosin, fluoresceins (and their derivatives), flavins, merocyanine 540; photoactive compounds, such as bergapten; and SE peptide. In addition, atoms which bind to prions, and thereby increase their sensitivity to inactivation by radiation, may also be used. An illustrative example of such an atom would be the Copper ion, which binds to the prion protein and, with a Z number higher than the other atoms in the protein, increases the probability that the prion protein will absorb energy during irradiation, particularly gamma irradiation.

As used herein, the term "radiation" is intended to mean radiation of sufficient energy to sterilize at least some component of the irradiated biological material. Types of radiation include, but are not limited to, the following: (i) corpuscular (streams of subatomic particles such as neutrons, electrons, and/or protons); (ii) electromagnetic (originating in a varying electromagnetic field, such as radio waves, visible (both mono and polychromatic) and invisible light, infrared, ultraviolet radiation, x-radiation, and gamma rays and mixtures thereof); and (iii) sound and pressure waves. Such radiation is often described as either ionizing (capable of producing ions in irradiated materials) radiation, such as gamma rays, and non-ionizing radiation, such as visible light. The sources of such radiation may vary and, in general, the selection of a specific source of radiation is not critical provided that sufficient radiation is given in an appropriate time and at an appropriate rate to effect sterilization. In practice, gamma radiation is usually produced by isotopes of Cobalt or Cesium, while UV and X-rays are produced by machines that emit UV and X-radiation, respectively, and electrons are often used to sterilize materials in a method known as "E-beam" irradiation that involves their production via a machine. Visible light, both mono- and polychromatic, is produced by machines and may, in practice, be combined with invisible light, such as infrared and UV, that is produced by the same machine or a different machine.

As used herein, the term "tissue" is intended to mean a substance derived or obtained from a multi-cellular living organism that performs one or more functions in the organism or a recipient thereof. Thus, as used herein, a "tissue" may be an aggregation of intercellular substance(s), such as collagen, elastin, fibronectin, fibrin, glycosaminoglycans and the like, and/or cells which are generally morphologically similar, such as hemapoietic cells, bone cells and the like. Accordingly, the term "tissue" is intended to include both allogenic and autologous tissue, including, but not limited to, cellular viable tissue, cellular non-viable tissue and acellular tissue, such as collagen, elastin, fibronectin, fibrin, glycosaminoglycans and the like. As used herein, the term "tissue" includes naturally occurring tissues, such as tissues removed from a living organism and used as such, or processed tissues, such as tissue processed so as to be less antigenic, for example allogenic tissue intended for transplantation, and tissue processed to allow cells to proliferate into the tissue, for example demineralised bone matrix that has been processed to enable bone cells to proliferate into and through it or heart valves that have been processed to encourage cell engraftment following implantation. Additionally, as used herein, the term "tissue" is intended to include natural, artificial, synthetic, semi-synthetic or semi-artificial materials comprised of biomolecules structured in such a way as to permit the replacement of at least some function(s) of a natural tissue when implanted into a recipient. Such constructs may be placed in a cell-containing environment prior to implantation to encourage their cellularization. Illustrative examples of tissues that may be treated according to the methods of the present invention include, but are not limited to, the following: connective tissue; epithelial tissue; a dipose tissue; cartilage, bone (including demineralised bone matrix); muscle tissue; and nervous tissue. Non-limiting examples of specific tissues that may be treated according to the methods of the present invention include heart, lung, liver, spleen, pancreas, kidney, corneas, joints, bone marrow, blood cells (red blood cells, leucocytes, lymphocytes, platelets, etc.), plasma, skin, fat, tendons, ligaments, hair, muscles, blood vessels (arteries, veins), teeth, gum tissue, fetuses, eggs (fertilized and not fertilized), eye lenses, hands, nerve cells, nerves, and other physiologically and anatomically complex tissues, such as intestine, cartilage, entire limbs, cadavers, and portions of brain, and intracellular substances, such as collagen, elastin, fibrinogen, fibrin, fibronectin, glycosaminoglycans, and polysaccharides.

As used herein, the term "to protect" is intended to mean to reduce any damage to the biological material being irradiated, that would otherwise result from the irradiation of that material, to a level that is insufficient to preclude the safe and effective use of the material following irradiation. In other words, as ubstance or process "protects" a biological material from radiation if the presence of that substance or carrying out that process results in less damage to the material from irradiation than in the absence of that substance or process. Thus, a biological material may be used safely and effectively after irradiation in the presence of a substance or following performance of a process that "protects" the material, but could not be used with as great a degree of safety or as effectively after irradiation under identical conditions but in the absence of that substance or the performance of that process.

As used herein, an "acceptable level" of damage may vary depending upon certain features of the particular method(s) of the present invention being employed, such as the nature and characteristics of the particular biological material and/or non-aqueous solvent(s) being used, and/or the intended use of the material being irradiated, and can be determined empirically by one skilled in the art. An "unacceptable level" of damage would therefore be a level of damage that would preclude the safe and effective use of the biological material being sterilized. The particular level of damage in a given biological material may be determined using any of the methods and techniques known to one skilled in the art.

B. Particularly Preferred Embodiments

A first particularly preferred embodiment of the present invention is directed to a device for measuring the amount of energy absorbed by a product undergoing sterilization with radiation, comprising: (i) an effective amount of at least one material that absorbs radiation in a quantifiable manner; and (ii) an effective amount of at least one cooling agent for maintaining said material within a predetermined temperature range between −120° C. and ambient temperature during irradiation.

Suitable materials that absorb radiation in a quantifiable manner are known and available to those skilled in the art. Preferred materials for use in the devices of the present invention include materials which, when irradiated, exhibit a reproducible change in some quantifiable property, e.g, a physical or chemical property of the material, that is related to the amount of radiation absorbed by the material. For example, suitable materials may exhibit changes in absorption spectra, luminescence, or free radical generation.

The change in the quantifiable property of the material may be measured using any of the methods and techniques known to those skilled in the art, such as spectrophotometry, spectrometry and micrometry. Illustrative examples of suitable techniques for use with the devices of the present invention include, but are not limited to, electron spin resonance (ESR) spectroscopy, UV spectrophotometry, electrochemical potentiation, color titration, UV/VIS spectrophotometry and colorimetry.

Illustrative examples of suitable materials that may be used in the devices of the present invention include, but are not limited to, alanine, cellulose acetate, ceric/cerous sulfate, potassium/silver dichromate, ferrous sulfate, radiochromic dye solutions, ethanol chlorobenzene, triphenyl methyl cyanide, crystalline solids such as alkali halides (e.g., LiF and the like) and radiochromic films.

In particularly preferred embodiments of the present invention, the material that absorbs radiation in a quantifiable manner is selected from among the following: alanine, cellulose acetate, ethanol chlorobenzene and radiochromic films.

The material which absorbs radiation in a quantifiable manner may be employed in the inventive device alone, for example, as pellets (such as alanine pellets). Alternatively, a plurality of different materials which absorb radiation in a quantifiable manner may be employed in combination. Suitable a mounts of such material(s) may be determined empirically by one skilled in the art.

According to still other preferred embodiments of the present invention, the material (or materials) that absorbs radiation may be mixed with one or more other suitable ingredients, such as binders and the like. The relative amounts of the material which absorbs radiation and any other ingredients that may be present, such as a binder, may be determined empirically by one skilled in the art using methods and techniques known in the art.

The material(s) that absorbs radiation in a quantifiable manner, and any other ingredients that may be present, may be formulated using any of the methods and materials known and available to those skilled in the art. For example, the material(s), and any other ingredient(s), may be molded, extruded or otherwise shaped or formed into a shape suitable for use in the devices of the present invention.

Illustrative examples of suitable binders that may be employed in devices according to certain preferred embodiments of the present invention include, but are not limited to, natural rubber, synthetic rubber and mixtures thereof. Illustrative examples of suitable synthetic rubbers include, but are not limited to, ethylene propylene copolymer, ethylene-vinyl acetate copolymer, chloroprene rubber, nitrile rubber, butyl rubber, synthetic isoprene rubber, styrene-butadiene copolymer, styrene-butadiene-acrylonitrile copolymer, butadiene rubber, acrylic rubber, urethane rubber, silicone rubber, polyisobutylene, polyester rubber, epichlorohydrin rubber and tetrafluoroethylene-propylene alternating copolymer.

Still other illustrative examples of suitable binders include polymers, such as ethylene-propylene copolymers, polyethylene, including low density polyethylene and very low density polyethylene, polyisobutylene, polyethylene terephthalates, polyamides, ethylene-vinyl acetate copolymers, polypropylene, polymethylmethacrylate (PMMA), methyl pentene, polycarbonate, polystyrene thermoset polymers, fluoropolymers, such as teflon and the like. Mixtures of such polymers may also be employed as the binder in the devices of the present invention.

Suitable cooling agents that may be employed in the devices of the present invention include any material capable of maintaining the material that absorbs radiation in a quanifiable manner within the predetermined temperature range. Such materials may be a solid or semi-solid, and may be in the form of particles, sheets, pellets and the like.

Illustrative examples of suitable cooling agents include, but are not limited, the following: dry ice, water ice, combinations of dry ice and non-aqueous solvents (also know as "dry ice baths"), such as methanol, ethanol, isopropanol, ethylene glycol (alone or thinned with water or isopropanol), acetone, dichloromethane, chloroform, carbon tetrachloride and the like. Such cooling agents may be used alone or in combination.

In certain particularly preferred embodiments of the present invention, the cooling agent is dry ice. According to these embodiments of the present invention, the cooling agent is preferably in the form of particles. Preferably, the particles of cooling agent have an average volume of not more than 17 cm$^3$ (about 1 in$^3$). More preferably, the particles of cooling agent have an average volume of not more than 1 cm$^3$ and even more preferably not more than 0.5 cm$^3$.

According to certain preferred embodiments of the present invention, the cooling agent is of sufficient volume to contain at least a portion of the material that absorbs radiation. For example, in a particularly preferred embodiment of the present, the cooling agent may be in the form of a block of dry ice with an opening sufficiently large to hold at least a portion of the material that absorbs radiation. Such an opening, e.g. a hole or depression in the block, may be drilled or otherwise prepared and then at least a portion of the material that absorbs radiation may be placed in that opening. Such openings may have any shape suitable to hold at least a portion of the material that absorbs radiation, such as rectangular, circular, square and the like. Preferably, the opening is of a sufficient size to contain substantially all of the material that absorbs radiation.

According to still other preferred embodiments of the present invention, the device for measuring the amount of energy absorbed by a product undergoing irradiation also includes a container of sufficient volume to contain at least a portion of the cooling agent and at least a portion of the material that absorbs radiation. Preferably, such a container is of sufficient volume to contain at least a portion of the cooling agent and substantially all of the material that absorbs radiation. Suitable containers include, but are not limited to, vacuum Dewars and other insulating containers, such as, polystyrene containers and the like.

In accordance with the various embodiments of the present invention, the cooling agent is capable of maintaining the material that absorbs energy in a quantifiable manner within a predetennined temperature range during irradiation of the material. Preferably, the temperature range is between about −120° C. and ambient temperature.

A second particularly preferred embodiment of the present invention is directed to a method for determining the amount of energy absorbed by a product undergoing sterilization with radiation. According to such preferred embodiments of the present invention, such methods include placing within a suitable container at least one product to be sterilized and at least one device, wherein the device comprises at least one material that absorbs radiation in a quantifiable manner and an effective amount of at least one cooling agent for maintaining the material within a predetermined temperature range, preferably between about −120° C. and ambient temperature, during irradiation; irradiating the container containing the product and the device; and analyzing the material that absorbs energy to determine the amount of energy absorbed during irradiation.

A third particularly preferred embodiment of the present invention is directed to a method for maintaining the temperature of a product undergoing irradiation within a predetermined temperature range, preferably between about −120° C. and ambient temperature. According to such preferred embodiments of the present invention, the method includes placing at least one product to be irradiated in a suitable container having at least one side and a bottom, wherein the volume defined by the container is greater than the volume of the product; placing an effective amount of at least one cooling agent in the container between the product and the at least one side; and irradiating the container containing the product and the cooling agent with ionizing radiation.

According to certain preferred embodiments of the present invention, the product being irradiated may be a biological material. According to other preferred embodiments of the present invention, the product may be a material that absorbs radiation in a quantifiable manner. In either such embodiment, the product is preferably frozen.

According to certain preferred embodiments of the present invention, the product may be a biological material selected from the group consisting of dextrose; urokinase; thrombin; trypsin; antithrombin III; plasminogen; plasma; purified protein fraction; blood; blood cells; alpha 1 proteinase inhibitor; digestive enzymes, such as galactosidases and sulfatases; blood proteins, such as albumin, Factor VIII, Factor VII, Factor IV, fibrinogen, monoclonal immunoglobulins and polyclonal immunoglobulins; and tissue, such as heart valves, ligaments, demineralized bone matrix, tendons, nerves, bone, teeth, bone marrow, skin grafts, cartilage, corneas, arteries, veins and organs for transplantation.

According to certain preferred embodiments of the present invention, the container having at least one side and a bottom may be a vacuum Dewar or a foam box, such as a polystyrene foam box.

In still other preferred embodiments of the present invention, this container having at least one side and a bottom may include a front side and a back side and a first side and a second side. According to such embodiments, the cooling agent is preferably placed between the product being irradiated and the first side and/or between the product being irradiated and the second side.

According to the methods of the present invention, any suitable radiation dose may be employed. According to preferred embodiments, such as when the product includes a biological material, the radiation dose is sufficient for sterilization.

According to the methods of the present invention, the predetermined temperature range is within the range of −120° C. to ambient temperature. In preferred embodiments of the present invention, both endpoints of the predetermined temperature range are less than ambient temperature.

According to other preferred embodiments of the present invention, at least one of the endpoints of the predetermined temperature range is less than the freezing point of the product being irradiated. More preferably, both endpoints of the temperature range are less than the freezing point of the product being irradiated.

According to still other preferred embodiments of the present invention, at least one endpoint of the predetermined temperature range is less than the glass transition temperature of the product being irradiated. In still other preferred embodiments of the present invention, both endpoints of the temperature range are less than the glass transition temperature of the product.

In certain preferred embodiments of the present invention, at least one of the endpoints of the predetermined temperature range is preferably less than −20° C., more at least one endpoint is preferably less than about −40° C., still more preferably at least one endpoint is less than about −60° C., and most preferably at least one endpoint is less than about −70° C.

In still other preferred embodiments of the present invention, both endpoints of the predetermined temperature range are less than about −20° C., more preferably both endpoints are less than about −40° C., still more preferably both endpoints are less than about −60° C., and most preferably both endpoints are less than about −70° C.

In certain other preferred embodiments of the present invention, the predetermined temperature range is less than the increase in temperature that would occur under adiabatic conditions.

According to other preferred embodiments of the present invention, the predetermined temperature range is less than 10° C. More preferably, the predetermined temperature range is less than 5° C., still more preferably the predetermined temperature range is less than about 2° C., even more preferably the predetermined temperature range is less than about 1.25° C., still even more preferably the predetermined temperature range is less than about 0.65° C., yet even still more preferably the predetermined temperature range is less than about 0.25° C., and most preferably the predetermined temperature range is less than about 0.1° C.

According to certain other preferred embodiments of the present invention, the predetermined temperature range is less than 0.1° C. per kGy (kiloGray) of radiation. More preferably, the predetermined temperature range is less than 0.05° C. per kGy of radiation, still more preferably the predetermined temperature range is less than about 0.02° C. per kGy of radiation, even more preferably the predetermined temperature range is less than about 0.0125° C. per kGy of radiation, and most preferably the predetermined temperature range is less than about 0.0065° C. per kGy of radiation.

The devices and methods of the present invention are particularly useful when employed in sterilization processes involving ionizing radiation, such as gamma radiation. For example, the devices and methods of the present invention may be used in conjunction with processes for sterilizing a preparation containing a biological material by subjecting that preparation to an effective amount of gamma radiation.

According to such preferred embodiments of the present invention, the preparation containing a biological material to be irradiated may be subjected to at least one, more preferably at least two, stabilizing processes prior to sterilization. Such stabilizing processes include, but are not limited to, adding to the preparation containing a biological material at least one stabilizer, reducing the residual solvent content of the preparation containing a biological material, reducing the temperature of the preparation containing a biological material, reducing the oxygen content of the preparation containing a biological material, maintaining or adjusting the pH of the preparation containing a biological material and adding to the preparation containing a biological material at least one non-aqueous solvent.

The preparation containing a biological material may contain a mixture of water and a non-aqueous solvent, such as ethanol and/or acetone. In such embodiments, the non-aqueous solvent(s) is (are) preferably a non-aqueous solvent that is not prone to the formation of free-radicals upon irradiation, and most preferably a non-aqueous solvent that is not prone to the formation of free-radicals upon irradiation and that has little or no dissolved oxygen or other gas(es) that is (are) prone to the formation of free-radicals upon irradiation. Volatile non-aqueous solvents are particularly preferred, even more particularly preferred are non-aqueous solvents that are also stabilizers, such as ethanol and acetone.

According to certain methods, a stabilizer is added prior to irradiation of the preparation containing a biological material with radiation. This stabilizer is preferably added to the preparation containing a biological material in an amount that is effective to protect the preparation containing a biological material from the radiation. Alternatively, the stabilizer is added to the preparation containing a biological material in an amount that, together with a non-aqueous solvent, is effective to protect the preparation containing a biological material from the radiation. Suitable amounts of stabilizer may vary depending upon certain features of the particular method(s) of the present invention being employed, such as the particular stabilizer being used and/or the nature and characteristics of the particular preparation containing a biological material being irradiated and/or its intended use, and can be determined empirically by one skilled in the art.

According to certain methods, the residual solvent content of the preparation containing a biological material is reduced prior to irradiation. The residual solvent content is preferably reduced to a level that is effective to protect the preparation containing a biological material from the radiation. Suitable levels of residual solvent content may vary depending upon certain features of the particular method(s) of the present invention being employed, such as the nature and characteristics of the particular preparation containing a biological material being irradiated and/or its intended use, and can be determined empirically by one skilled in the art. There may be preparations containing biological materials for which it is desirable to maintain the residual solvent content to within a particular range, rather than a specific value.

According to certain methods, when the preparation containing a biological material also contains water, the residual solvent (water) content of the preparation containing a biological material may be reduced by dissolving or suspending the preparation containing a biological material in a non-aqueous solvent that is capable of dissolving water. Preferably, such a non-aqueous solvent is not prone to the formation of free-radicals upon irradiation and has little or no dissolved oxygen or other gas(es) that is (are) prone to the formation of free-radicals upon irradiation.

While not wishing to be bound by any theory of operability, it is believed that the reduction in residual solvent content reduces the degrees of freedom of the preparation containing a biological material, reduces the number of targets for free radical generation and may restrict the diffusability of these free radicals. Similar results might therefore be achieved by lowering the temperature of the preparations containing a biological material below their eutectic point(s) or below their freezing point(s), or by vitrification to likewise reduce the degrees of freedom of the preparation containing a biological material. These results may permit the use of a higher rate and/or dose of radiation than might otherwise be acceptable. Thus, the methods described herein may be performed at any temperature that doesn't result in unacceptable damage to the preparation containing a biological material, i.e., damage that would preclude the safe and effective use of the preparation containing a biological material. Preferably, the methods described herein are performed at ambient temperature or below ambient temperature, such as below the eutectic point(s) or freezing point(s) of the preparation containing a biological material being irradiated.

In certain embodiments, the desired residual solvent content of a particular preparation containing a biological material may be found to lie within a range, rather than at a specific point. Such a range for the preferred residual solvent content of a particular biological material may be determined empirically by one skilled in the art.

The residual solvent content of the preparation containing a biological material may be reduced by any of the methods and techniques known to those skilled in the art for reducing solvent from the preparation containing a biological material without producing an unacceptable level of damage to the preparation containing a biological material. Such methods include, but are not limited to, lyophilization, drying, concentration, addition of alternative solvents, evaporation, chemical extraction and vitrification.

A particularly preferred method for reducing the residual solvent content of a preparation containing a biological material is lyophilization.

Another particularly preferred method for reducing the residual solvent content of a preparation containing a biological material is vitrification, which may be accomplished by any of the methods and techniques known to those skilled in the art, including the addition of solute and or additional solutes, such as sucrose, to raise the eutectic point(s) of the preparation containing a biological material, followed by a gradual application of reduced pressure to the preparation containing a biological material in order to remove the residual solvent. The resulting glassy material will then have a reduced residual solvent content.

According to certain methods, the preparation containing a biological material to be sterilized may be immobilized upon or attached to a solid surface by any means known and available to one skilled in the art. For example, the preparation containing a biological material to be sterilized may be attached to a biological or non-biological substrate.

In another preferred embodiment, where the preparation containing a biological material contains oxygen or other gases dissolved within the preparation containing a biological material or within their container or associated with them, the amount of these gases within or associated with the preparation containing a biological material may be reduced by any of the methods and techniques known and available to those skilled in the art, such as the controlled reduction of pressure within a container (rigid or flexible) holding the preparation containing a biological material to be treated or by placing the preparation containing a biological material in a container of approximately equal volume.

In certain embodiments, when the preparation containing a biological material to be treated contains an aqueous or non-aqueous solvent, or a mixture of such solvents, at least one stabilizer is introduced according to any of the methods and techniques known and available to one skilled in the art, including soaking the tissue in a solution containing the stabilizer(s), preferably under pressure, at elevated temperature and/or in the presence of a penetration enhancer, such as dimethylsulfoxide, and more preferably, when the stabilizer(s) is a protein, at a high concentration. Other methods of introducing at least one stabilizer into tissue include, but are not limited to, the following: applying a gas containing the stabilizer(s), preferably under pressure and/or at elevated temperature; injecting the stabilizer(s) or a solution containing the stabilizer(s) directly into the tissue; placing the tissue under reduced pressure and then introducing a gas or solution containing the stabilizer(s); dehydrating the tissue, such as by using a buffer of high ionic and/or osmolar strength, and rehydrating the tissue with a solution containing the stabilizer(s); applying a high ionic strength solvent c ontaining the stabilizer(s), which may optionally be followed by a controlled reduction in the ionic strength of the solvent; cycling the tissue between solutions of high ionic and/or osmolar strength and solutions of low ionic and/or osmolar strength containing the stabilizer(s); and combinations of two or more of these methods. One or more sensitizers may also be introduced into tissue according to such methods.

According to certain embodiments, in order to enhance penetration of one or more stabilizers and/or sensitizers into the tissue, one or more compounds effective to increase penetration into the tissue may be employed. For instance, the tissue may treated with one or more compounds that cause an increase in the distance between molecules in the tissue, thereby promoting penetration of the stabilizers and/or sensitizers into the tissue.

Similarly, the tissue may be treated with one or more compounds that cause macromolecules in the tissue to become less compact, or relaxed, thereby promoting penetration of the stabilizer(s) and/or sensitizer(s) into the tissue or providing a greater surface area of tissue to be in contact with the stabilizer(s) and/or sensitizer(s). The compounds that cause macromolecules in the tissue to become less compact, or relaxed, may also be applied prior to introduction of the stabilizer(s) and/or sensitizer(s), which may then be introduced in a similar solution followed by application of a solution containing a similar amount of stabilizer(s) and/or sensitizer(s) but a reduced amount of the compounds that cause macromolecules in the tissue to become less compact, or relaxed. Repeated applications of such solutions, with progressively lower amounts of compounds that cause macromolecules in the tissue to become less compact, or relaxed, may subsequently be applied.

The compounds that promote penetration may be used alone or in combination, such as a combination of a compound that causes macromolecules in the tissue to become less compact and a compound that causes an increase in the distance between molecules in the tissue.

Further, in those embodiments wherein the stabilizer(s) and/or sensitizer(s) is cationic, one or more anionic compounds may be added to the solution containing the stabilizer(s) and/or sensitizer(s) prior to and/or during application thereof to the preparation containing a biological material. The anionic compound(s) may also be applied prior to introduction of the stabilizer(s) and/or sensitizer(s), which may then be introduced in a similar solution followed by application of a solution containing a similar amount of stabilizer(s) and/or sensitizer(s) but a reduced amount of the anionic compound(s). Repeated applications of such solutions, with progressively lower amounts of anionic compound(s) may subsequently be applied.

Similarly, in those embodiments wherein the stabilizer(s) and/or sensitizer(s) is anionic, one or more cationic compounds may be added to the solution containing the stabilizer(s) and/or sensitizer(s) prior to and/or during application thereof to the preparation containing a biological material. The cationic compound(s) may also be applied prior to introduction of the stabilizer(s) and/or sensitizer(s), which may then be introduced in a similar solution followed by application of a solution containing a similar amount of stabilizer(s) and/or sensitizer(s) but a reduced amount of the cationic compound(s). Repeated applications of such solutions, with progressively lower amounts of cationic compound(s) may subsequently be applied.

It will be appreciated that the combination of one or more of the features described herein may be employed to further minimize undesirable effects upon the preparation containing a biological material caused by irradiation, while maintaining adequate effectiveness of the irradiation process on the biological contaminant(s) or pathogen(s). For example, in addition to the use of a stabilizer, a particular preparation containing a biological material may also be lyophilized, held at a reduced temperature and kept under vacuum prior to irradiation to further minimize undesirable effects.

The radiation employed may be any radiation effective for the sterilization of the preparation containing a biological material being treated. The radiation may be corpuscular, including E-beam radiation. Preferably the radiation is electromagnetic radiation, including x-rays, infrared, visible light, UV light and mixtures of various wavelengths of electromagnetic radiation. A particularly preferred form of radiation is gamma radiation.

According to these preferred methods, the preparation containing a biological material is irradiated with the radiation at a rate effective for the sterilization of the preparation containing a biological material, while not producing an unacceptable level of damage to the preparation containing a biological material. Suitable rates of irradiation may vary depending upon certain features of the methods of the present invention being employed, such as the nature and characteristics of the particular preparation containing a biological material, which may contain a non-aqueous solvent, being irradiated, the particular form of radiation involved, and/or the particular biological contaminants or pathogens being inactivated. Suitable rates of irradiation can be determined empirically by one skilled in the art. Preferably, the rate of irradiation is constant for the duration of the sterilization procedure. When this is impractical or otherwise not desired, a variable or discontinuous irradiation may be utilized.

According to these methods, the rate of irradiation may be optimized to produce the most advantageous combination of product recovery and time required to complete the operation. Both low (<3 kGy/hour) and high (>3 kGy/hour) rates may be utilized in the methods described herein to achieve such results. The rate of irradiation is preferably selected to optimize the recovery of the preparation containing a biological material while still sterilizing the preparation containing a biological material. Although reducing the rate of irradiation may serve to decrease damage to the preparation containing a biological material, it will also result in longer irradiation times being required to achieve a particular desired total dose. A higher dose rate may therefore be preferred in certain circumstances, such as to minimize logistical issues and costs, and may be possible particularly when used in accordance with the methods described herein for protecting the preparation containing a biological material from irradiation.

According to particularly preferred methods, the rate of irradiation is not more than about 3.0 kGy/hour, more preferably between about 0.1 kGy/hr and 3.0 kGy/hr, even more preferably between about 0.25 kGy/hr and 2.0 kGy/hour, still even more preferably between about 0.5 kGy/hr and 1.5 kGy/hr and most preferably between about 0.5 kGy/hr and 1.0 kGy/hr.

According to other particularly preferred methods, the rate of irradiation is at least about 3.0 kGy/hr, more preferably at least about 6 kGy/hr, even more preferably at least about 16 kGy/hr, even more preferably at l east a bout 30 k Gy/hr and m ost preferably at l east a bout 45 kGy/hr or greater.

According to these methods, the preparation containing a biological material to be sterilized may be irradiated with the radiation for a time effective for the sterilization of the preparation containing a biological material. Combined with irradiation rate, the appropriate irradiation time results in the appropriate dose of irradiation being applied to the preparation containing a biological material. Suitable irradiation times may vary depending upon the particular form and rate of radiation involved and/or the nature and characteristics of the particular preparation containing a biological material being irradiated. Suitable irradiation times can be determined empirically by one skilled in the art.

According to these methods, the preparation containing a biological material to be sterilized is irradiated with radiation up to a total dose effective for the sterilization of the preparation containing a biological material, while not producing an unacceptable level of damage to those preparations containing a biological material. Suitable total doses of radiation may vary depending upon certain features of the methods of the present invention being employed, such as the nature and characteristics of the particular preparation containing a biological material being irradiated, the particular form of radiation involved, and/or the particular biological contaminants or pathogens being inactivated. Suitable total doses of radiation can be determined empirically by one skilled in the art. Preferably, the total dose of radiation is at least 25 kGy, more preferably at least 45 kGy, even more preferably at least 75 kGy, and still more preferably at least 100 kGy or greater, such as 150 kGy or 200 kGy or greater.

The particular geometry of the preparation containing a biological material being irradiated, such as the thickness and distance from the source of radiation, may be determined empirically by one skilled in the art. A preferred embodiment is a geometry that provides for an even rate of irradiation throughout the preparation containing a biological material. A particularly preferred embodiment is a geometry that results in a short path length for the radiation through the preparation, thus minimizing the differences in radiation dose between the front and back of the preparation. This may be further minimized in some preferred geometries, particularly those wherein the preparation containing a biological material has a relatively constant radius about its axis that is perpendicular to the radiation source and by the utilization of a means of rotating the preparation containing a biological material about said axis.

Similarly, according to certain methods, an effective package for containing the preparation containing a biological material during irradiation is one which combines stability under the influence of irradiation, and which minimizes the interactions between the package of the preparation containing a biological material and the radiation. Preferred packages maintain a seal against the external environment before, during and post-irradiation, and are not reactive with the preparation containing a biological material within, nor do they produce chemicals that may interact with the preparation containing a biological material within. Particularly preferred examples include but are not limited to containers that comprise glasses stable when irradiated, stoppered with stoppers made of rubber or other suitable materials that is relatively stable during radiation and liberates a minimal amount of compounds from within, and sealed with metal crimp seals of aluminum or other suitable materials with relatively low Z numbers. Suitable materials can be determined by measuring their physical performance, and the amount and type of reactive leachable compounds post-irradiation, and by examining other characteristics known to be important to the containment of such biological materials as preparation containing a biological material empirically by one skilled in the art.

According to certain methods, an effective amount of at least one sensitizing compound may optionally be added to the preparation containing a biological material prior to irradiation, for example to enhance the effect of the irradiation on the biological contaminant(s) or pathogen(s) therein, while employing the methods described herein to minimize the deleterious effects of irradiation upon the preparation containing a biological material. Suitable sensitizers are known to those skilled in the art, and include psoralens and their derivatives and inactines and their derivatives.

According to these methods, the irradiation of the preparation containing a biological material may occur at any temperature below ambient, such as 0° C., −20° C., −40° C., −60° C., −70° C. or −78° C. According to this embodiment, the preparation containing a biological material is preferably irradiated at or below the freezing or eutectic point(s) of the preparation containing a biological material or the residual solvent therein. Most preferably, the irradiation of the preparation containing a biological material occurs at a temperature that protects the preparation containing a biological material from radiation. Suitable temperatures can be determined empirically by one skilled in the art.

In certain embodiments, the temperature at which irradiation is performed may be found to lie within a range, rather than at a specific point. Such a range for the preferred temperature for the irradiation of a particular preparation containing a biological material may be determined empirically by one skilled in the art.

According to these methods, the irradiation of the preparation containing a biological material may occur at any pressure which is not deleterious to the preparation containing a biological material being sterilized. According to one preferred embodiment, the preparation containing a biological material is irradiated at elevated pressure. More preferably, the preparation containing a biological material is irradiated at elevated pressure due to the application of sound waves or the use of a volatile. While not wishing to be bound by any theory, the use of elevated pressure may enhance the effect of irradiation on the biological contaminant(s) or pathogen(s) and/or enhance the protection afforded by one or more stabilizers, and therefore allow the use of a lower total dose of radiation. Suitable pressures can be determined empirically by one skilled in the art.

Generally, according to these methods, the pH of the preparation containing a biological material undergoing sterilization is about 7. In some embodiments, however, the preparation containing a biological material may have a pH of less than 7, preferably less than or equal to 6, more preferably less than or equal to 5, even more preferably less than or equal to 4, and most preferably less than or equal to 3. In alternative embodiments, the preparation containing a biological material may have a pH of greater than 7, preferably greater than or equal to 8, more preferably greater than or equal to 9, even more preferably greater than or equal to 10, and most preferably greater than or equal to 11. According to certain embodiments, the pH of the preparation containing a biological material undergoing sterilization is at or near the isoelectric point of one of the components of the preparation containing a biological material. Suitable pH levels can be determined empirically by one skilled in the art.

Similarly, according to these methods, the irradiation of the preparation containing a biological material may occur under any atmosphere that is not deleterious to the preparation containing a biological material being treated. According to one preferred embodiment, the preparation containing a biological material is held in a low oxygen atmosphere or an inert atmosphere. When an inert atmosphere is employed, the atmosphere is preferably composed of a noble gas, such as helium or argon, more preferably a higher molecular weight noble gas, and most preferably argon. According to another preferred embodiment, the preparation containing a biological material is held under vacuum while being irradiated. According to a particularly preferred embodiment, the preparation containing a biological material (lyophilized, liquid or frozen) is stored under vacuum or an inert atmosphere (preferably a noble gas, such as helium or argon, more preferably a higher molecular weight noble gas, and most preferably argon) prior to irradiation. According to an alternative preferred embodiment, the preparation containing a biological material is held under low pressure, to decrease the amount of gas, particularly oxygen and nitrogen, dissolved in the liquid, prior to irradiation, either with or without a prior step of solvent reduction, such as lyophilization. Such degassing may be performed using any of the methods known to one skilled in the art. For example, the preparation containing a biological material may be treated prior to irradiation with at least one cycle, and preferably three cycles, of being subjected to a vacuum and then being placed under an atmosphere comprising at least one noble gas, such as argon, or nitrogen.

The sensitivity of a particular biological contaminant or pathogen to radiation is commonly calculated by determining the dose necessary to inactivate or kill all but 37% of the agent in a sample, which is known as the $D_{37}$ value. The desirable components of a preparation containing a biological material may also be considered to have a $D_{37}$ value equal to the dose of radiation required to eliminate all but 37% of their desirable biological and physiological characteristics.

In accordance with certain preferred methods, the sterilization of the preparation containing a biological material is conducted under conditions that result in a decrease in the $D_{37}$ value of the biological contaminant or pathogen without a concomitant decrease in the $D_{37}$ value of the preparation containing a biological material. In accordance with other preferred methods, the sterilization of the preparation containing a biological material is conducted under conditions that result in an increase in the $D_{37}$ value of the preparation containing a biological material. In accordance with the most preferred methods, the sterilization of the preparation containing a biological material is conducted under conditions that result in a decrease in the $D_{37}$ value of the biological contaminant or pathogen and a concomitant increase in the $D_{37}$ value of the preparation containing a biological material.

In accordance with certain preferred methods, the sterilization of the preparation containing a biological material is conducted under conditions that reduce the possibility of the production of neo-antigens. In accordance with other preferred embodiments, the sterilization of the preparation containing a biological material is conducted under conditions that result in the production of substantially no neo-antigens.

In accordance with certain preferred methods, the sterilization of the preparation containing a biological material is conducted under conditions that reduce the total antigenicity of the preparation containing a biological material. In accordance with other preferred embodiments, the sterilization of preparation containing a biological material is conducted under conditions that reduce the number of reactive allo-antigens and/or xeno-antigens in the preparation containing a biological material.

According to certain preferred embodiments, preparation containing a biological material sterilized according to the methods described herein may be introduced into a mammal in need thereof for prophylaxis or treatment of a condition or disease or malfunction of a tissue. Methods of introducing such preparation containing a biological material into a mammal are known to those skilled in the art.

When employed in such embodiments, preparation containing a biological material sterilized according to the methods described herein do not produce sufficient negative characteristics in the preparation containing a biological material following introduction into the mammal to render the preparation containing a biological material unsafe and/or ineffective for the intended use thereof. Illustrative examples of such negative characteristics include, but are not limited to, inflammation and calcification. Such negative characteristics may be detected by any means known to those skilled in the art, such as MRIs, CAT scans and the like.

According to particularly preferred embodiments, sterilization of the preparation containing a biological material is conducted after the preparation containing a biological material is packaged, i.e. as a terminal sterilization process.

EXAMPLES

Example 1

Paste Experiment

Figure 2:
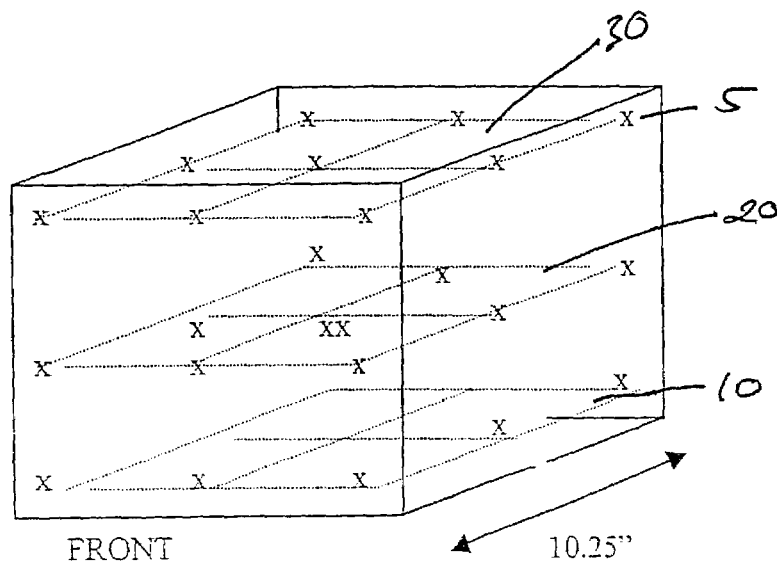
FIG. 2 shows the placement of alanine dosimeters in a device according to a preferred embodiment of the present invention.

Purpose: To evaluate dose distribution and temperature profile for a volume of bovine paste gamma irradiated in an insulated container. In this experiment, an insulated container (24" H×23.75" W×23.57" L) containing frozen bovine paste (14" H×10.5" W×10.25" L) and dry ice was irradiated with gamma irradiation in a carrier batch facility (FIG. 1). Irradiation was carried out in two unequal dose fractions to a specified surface dose. Thermocouples (TC's) and dosimeters were placed throughout the paste (FIG. 2). Thermal labels and dosimeters were placed externally on the insulated container (FIG. 3).

Equipment and Materials:

1. Omega Type T TC's (Stock #5SC-TT-T-36-72); 36 gauge wire, 72" length;
2. Omega TC Readers: Model HH202A (Serial No. 20910, reader 1; and Serial No. 20909, reader 2).
3. Envirocooler Insulated Container EVC-30-40-LL
   Outer Dimensions: 24" H×23.75" W×23.57" L
   Inner Dimensions: 17.5" H×17.75" W×17.75 " L
4. Cardboard Paste Container: 14" H×10.5" W×10.25" L
5. Dry Ice (pellets)
6. Bovine Fraction "A" Paste: Filter press paste (50–60% IgG), diatomaceous earth and Perlite, prepared using the Kistler & Nitschmann fractionation procedure
7. Dosimeters: Alanine pellets (Gamma Service, Batch T79801) and Red 4034 Perspex GH
8. 0.6 ml Microfuge Tubes
9. Cardboard Slip Sheets
10. Thermal Labels (Paper Thermometer Co., Set #10, 32.3-54.4° C.)
11. STERIS Batch-type Irradiator (IR-131), Whippany, N.J.

Procedure:

1. The functionality of the TC's using two readout instruments was assessed and each TC was uniquely identified. A 3-point verification at nominal temperatures of 22° C., 0° C. and −78° C. was used. Only TC's that performed to within 2° C. of reference temperature were used.
2. Prepared dosimeters. Each dosimeter consisted of three alanine dosimeters in a 0.6 ml Microfuge Tube. Each tube was uniquely labelled.
3. Dosimeters and TC's 5 were arranged on three cardboard slip sheets as shown in FIG. 2.
4. Envirocooler container was labelled Front, Rear and Top, as shown in FIG. 3.

5. Polyethylene bags were cut and glued to the interior surface of the paste carton to protect the cardboard surface from excess moisture.

6. As shown in FIG. 2, a first cardboard slip sheet 10 was placed in the bottom of the paste container and the paste container was filled to approximately mid-height with bovine paste. A second cardboard slip sheet 20 was placed on top of the bovine paste and the paste container was filled to the top with bovine paste. A third cardboard slip sheet 30 was placed on top of the bovine paste. The height of the second slip sheet relative to the first slip sheet was recorded. The height of the third slip sheet relative to the first and second slip sheets was recorded.

7. The carton was sealed with the TC leads for each slip sheet bundled together and extending from the container for subsequent temperature measurements.

8. The paste was frozen at −40° C. Once the paste was frozen, the paste container was measured and weighed.

9. Placed the paste container 40 in the Envirocooler 50, as shown in FIG. 1. The bundled TC leads were extended and secured to the surface of the Envirocooler.

10. Added cardboard sleeves 60 that extend from front to back of the Envirocooler 50.

11. Placed Styrofoam into the void spaces 80 to stabilizer the paste container in the Envirocooler 50.

12. Weighed the container.

13. Placed dry ice between the cardboard sleeves 60 and the sides of the Envirocooler 50.

14. Sealed the container.

Figure 3A:
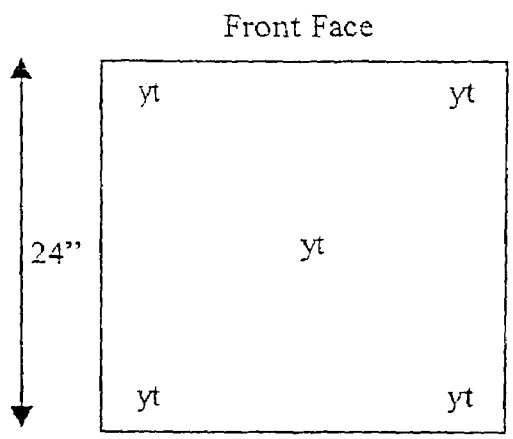
FIG. 3 shows the placement of alanine dosimeters and thermal tape on a device according to a preferred embodiment of the present invention.
Figure 3B:
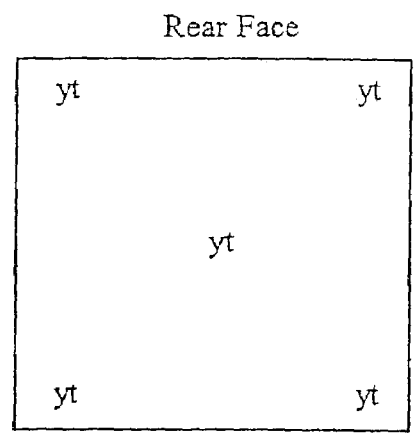
Figure 3C:
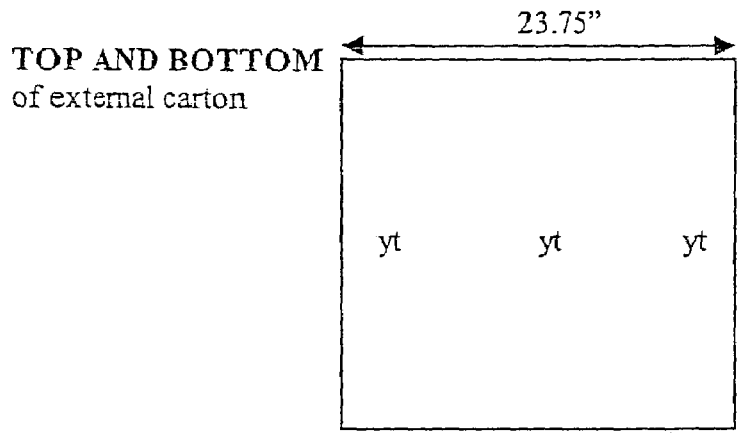

15. Positioned thermal tape and external dosimeters on the rear face, front face, top and bottom of the Envirocooler, as shown in FIGS. 3a–3c.

16. Just prior to irradiation, measured temperature at each TC.

17. Placed the container in the carrier on top of about 32" of cardboard, such that the front and rear faces of the container were parallel to the source plaque.

18. Placed about 4" of cardboard on top of the container.

19. Irradiated the container to achieve a surface dose of 50 kGy (dose in water) in two unequal dose portions.

20. Following each dose portion, recorded the temperature for each TC.

21. After the final dose portion, removed the container from the carrier, removed external dosimeters, weighed the container and recorded the thermal label results.

Results:

| Weight Summary: | |
| --- | --- |
| Item | Weight (lbs.) |
| Envirocooler (empty) | 17.2 |
| Paste Carton (filled) | 42.2 |
| Dry Ice | |
| Start | 63.6 |
| End | 40.0 |
| Total Weight (packed container) | 123 |

Maximum recorded temperatures ranged from 38° C. to 54° C. (approximately a 15 to 30° C. rise for all labels). Front face labels ranged from 49 to 54° C. while rear face labels ranged from 38 to 43° C. Top and bottom labels read 38° C. Temperature were observed to have reached the maximum reported values during the first radiation dose fraction.

According to the TC measurements, temperatures within the paste, generally, rose about 15° C. or less. The minimum dose received by the paste, 37.4 kGy, occurred at the geometric center, while the maximum dose received by the paste, 55.4 kGy, occurred at the rear top center position. The dose drop off from the front or rear center position to the midsection center position was approximately 30% (±15%). Alanine doses were consistently higher than the corresponding Red 4034 dose values.

The Envirocooler container (3" thick) and dry ice arrangement provided temperature control throughout all stages of preparation, irradiation and post-irradiation handling.

Example 2

Purpose: To test the ability of two devices to maintain the temperature of an alanine pellet at dry ice temperature while being exposed to gamma irradiation.

Materials and Equipment:

1. Wheaton 120 cc bottles (Catalog #225546, Lot #1208867-01) with dimension 4" high ×1.75" diameter.

2. Dry ice blocks and pellets-Artic Ice

3. Craftsman cordless power drill

4. Cheesecloth

5. Hammer

6. Glue stick

7. Omega Engineering Type T, 36 AWG, 72" long wire, Teflon insulated Thermocouples (Catalog #5SC-TT-T-36-72)- numbered 1 through 4.

8. Omega Engineering thermocouple extension cables SMP female to SMP male, 10 ft long (Catalog #TECT-10-9)

9. Temperature Recording Device High Precision Temperature and Voltage Meter: National Instruments Model NI 4350, Part #184374C-01, SN CD2141
   a. Analog Input device: National Instruments Model TC 2190, Part #184473B-10, SN CB2154
   b. Dell laptop computer with Virtual Bench Logger software program 10. Gamma Irradiation Facility: Gammacell 207, National Institutes of Standards and Technology, Radiation Physics Building #245, Gaithersburg, Md.

11. Vacuum Dewar Flask- Cole Palmer Stainless Steel Dewar Flask Series 3763 Cat# D1000W, 1L volume, 16 cm inner height, 10 cm diameter (provided by NIST)

12. Cork cover- Cole Palmer D1000W Cat#03763-32 (provided by NIST)

Procedure:

1. Trimmed excess foil packaging on two (2) alanine pellet blister pack to ~½" square.

2. Cut block dry ice slab to make a piece with dimensions ~4"×1.5"×1.5" (H×D ×W).

3. Using a drill, fashioned a ½" square slot (~⅛"tall) into one side of a dry ice block at vertical center (~2"from the top). Stored in insulated cooler with dry ice to minimize sublimation prior to irradiation.

4. With sample chamber in "up" position (i.e. not irradiating) positioned four (4) thermocouples (TC) junctions (#1 thru #4) into the sample chamber of the gammacell 207 with the plugs accessible to the external environment.

5. Attached TC extensions and set-up temperature recording device.

6. Began temperature data acquisition of TC#1 through #4.

7. Using cheesecloth and hammer, pulverized pelleted dry ice into a fine powder.

8. Set-up of "Block Dry Ice" alanine temperature control device:
   a. Using a needle, made a small hole in the alanine blister pack.
   b. Fed TC#1 junction and wire into the alanine blister pack such that TC#1 junction was in contact with the alanine pellet.
   c. Positioned alanine blister pack-thermocouple #1 assembly into the air space created in the block form of dry ice (bubble side facing down).
   d. Placed block dry ice into vacuum dewar with TC wire extending out of the top of the dewar.
9. Set-up of "Powdered dry ice—Bottle" alanine temperature control device:
   a. Filled one 120 cc glass bottle with ~½ powdered dry ice and packed down using glue stick.
   b. Fed TC#2 junction and wire into the alanine blister pack such that TC#2 junction was in contact with the alanine pellet.
   c. Positioned alanine blister pack-thermocouple #2 assembly into the approximate center of the 120 cc bottle (bubble side facing down).
   d. Placed powdered dry ice-bottle assembly into vacuum dewar with TC wire extending out of the top of the dewar.
10. Positioned TC#3 inside the dewar such that it would record the temperature of the air space (i.e. not in contact with the bottle surface or block dry ice).
11. Placed cork lid onto top of dewar.
12. Positioned dewar in the gammacell sample chamber.
13. Positioned TC#4 in the sample chamber such that it would record the temperature of the air space in the sample chamber.
14. Allowed TCs to equilibrate for ~10–15 minutes until TC #1 and #2 stabilized to a reading of approximately −78° C.
15. Started irradiation and noted temperatures of all TCs.
16. Ended irradiation and noted temperature of all TCs.'
17. Total Irradiation time was 6.148 hours. Based on estimated dose rate, total delivered dose was 105.84 kGy.
18. Disassembled vacuum dewar and alanine temperature control devices. Noted the amount of dry ice remaining for each device.

Results:

The temperature in the near proximity of the alanine pellet increased 1.25° C. in the block dry ice device for six hours while the pellet was exposed to approximately 105 kGy of gamma irradiation at a dose rate of approximately 17.2 kGy/hr.

The temperature in the near proximity of the alanine pellet increased 0.65° C. in the powdered dry ice-bottle device for six hours while the pellet was exposed to approximately 105 kGy of gamma irradiation at a dose rate of approximately 17.2 kGy/hr.

At least 50% of the dry ice remained in the devices (either solid or powdered) following gamma irradiation.

Conclusion:

The temperature of an alanine dosimeter can be maintained to within +1.25° C. of its starting dry ice temperature (−78° C.) during a six hour exposure to gamma irradiation (−105 kGy total dose) when positioned in the either of a 120 cc bottle filled with powdered dry ice or a block of solid dry ice (approx. dimensions 4"×1.5"×1.5"). A temperature summary is presented in Table 1.

TABLE 1

Temperature Summary

| TC # | Description | Initial Temperature | Final Temperature | Change in Temperature during Irradiation |
|---|---|---|---|---|
| 1 | Block Dry Ice | −78.009° C. | −76.75° C. | +1.25° C. |
| 2 | Powdered Dry Ice-Bottle | −78.088° C. | −77.44° C. | +0.648° C. |
| 3 | Dewar Air Space | −71.684° C. | −66.313° C. | +5.371° C. |
| 4 | Sample Chamber Air Space | 27.393° C. | 55.84° C. | +28.447° C. |

Example 3

Purpose: To test the ability of a small glass Dewar to maintain the temperature of an alanine pellet while being exposed to gamma irradiation.

Meterial and Equipment:
1. Vacuum Dewar, Silvered, 22 mm OD×12.6 mm ID—H. S. Martin, Inc.
2. Styrofoam plug
3. Dry ice blocks and pellets-Artic Ice
4. Craftsman cordless power drill
5. Plug-cutter—½" Irwin #43908
6. 50 ml polypropylene tube
7. Harwell Batch AC Alanine pellets, heat sealed individually into foil-laminate pouches.
8. Omega Engineering Type T, 36 AWG, 72" long wire, Teflon insulated Thermocouples (Catalog #5SC-TT-T-36-72).
9. Omega Engineering thermocouple extension cables SMP female to SMP male, 10 ft long (Catalog # TECT-10-9)
10. Bruker EPR Spectrometer (eScan) system
    a. Electronics Unit (Model E2043000, Serial No. 0133)
    b. Magnetic Unit (Model E2044000, Serial No. 0133)
    c. Pellet Probe PH0019
11. Denver M-220 analytical (micro) balance (Serial No. P112332)
12. Temperature Recording Device
    a. High Precision Temperature and Voltage Meter: National Instruments Model NI 4350, Part # 184374C-01, SN CD2141
    b. Analog Input device: National Instruments Model TC 2190, Part # 184473B-10, SN CB2154
    c. Dell laptop computer with Virtual Bench Logger software program
13. Gamma Irradiation Facility: Gamma cell 207, National Institutes of Standards and Technology, Radiation Physics Building #245, Gaithersburg, Md.
14. Vacuum Dewar Flask—Cole Palmer Stainless Steel Dewar Flask Series 3763 Cat# D1000W, 1 L volume, 16 cm inner height, 10 cm diameter (provided by NIST)
15. Cork cover—Cole Palmer D1000W Cat#03763-32 (provided by NIST)

Procedure:
1. Pre-cooled micro Dewar in dry ice for 30–60 min.
2. Taped alanine pellet in foil-laminate pouch onto outside of Dewar.
3. With sample chamber in "up" position (i.e. not irradiating) positioned three (3) thermocouples (TC) junctions (#1, #2, and #3) into the sample chamber of the gamma cell 207 with the plugs accessible to the external environment.

4. Attached TC extensions and set-up temperature recording device.

5. Began temperature data acquisition.

6. Pre-cooled the stainless stain Dewar by filling it with pelleted dry ice (~30min)

7. Prepared solid dry ice "plugs" for use in the Dewar.

8. Using lab tape, secured TC#1 with an alanine pellet in foil-laminate pouch bottle surface or block dry ice.

9. Filled the micro Dewar ~½ full with dry ice plugs.

10. Place alanine pellet/TC#1 packet into the Dewar and tapped down using a pen to make contact with the dry ice.

11. Added dry ice pellets on top of alanine pellet/TC#1 and tapped down using a pen.

12. Covered the Dewar opening with a Styrofoam plug.

13. Placed Dewar in 50 ml polypropylene tube.

14. Secured TC#2 in the air space between the micro Dewar and the 50 ml tube.

15. Placed cork lid onto top of stainless steel Dewar.

16. Positioned stainless steel Dewar in the gamma cell sample chamber.

17. Allowed TCs to equilibrate for ~10–15 minutes until TC #1 and #2 stabilized to a reading of approximately −78° C.

18. Started irradiation and noted temperature of all TCs.

19. Ended irradiation and noted temperature of all TCs.

20. Total irradiation time was 5 hours, 53 minutes, 34 seconds. Based on estimated dose rate, total delivered dose was 99.23 kGy.

21. Disassembled vacuum Dewar and alanine temperature control devices. Noted the amount of dry ice remaining in the micro Dewar.

22. Compute the absorbed dose to both alanine pellets.

Results:

The temperature in the near proximity of the alanine pellet increased 1.9° C. in the micro Dewar while the pellet was exposed to approximately six hours of gamma irradiation at a dose rate of approximately 16.8 kGy/hr. Approximately 50% of the dry ice remained in the micro Dewar device following gamma irradiation.

Conclusions:

The temperature of an alanine dosimeter can be maintained to within 2° C. of its starting dry ice temperature (−78° C.) during six hours exposure to gamma irradiation (~100 kGy total dose) when positioned in the center of a small glass vacuum Dewar. A temperature is presented in Table 2.

TABLE 2

Temperature Summary

| TC # | Description | Initial Temperature | Final Temperature | Change in Temperature during Irradiation | Average Temperature during the irradiation |
|---|---|---|---|---|---|
| 2 | Alanine Pellet inside Dewar | −78.12° C. | −76.227° C. | +1.9° C. | −77 |
| 3 | Alanine Pellet outside Dewar | −78.992° C. | −73.877° C. | +5.1° C. | −76.005 |

Example 4

Purpose: To perform qualitative and quantitative analyses of Harwell alanine pellet dosimeters with respect to reproducibility (evaluating replicate samples irradiated to known dose levels), calibration (determination of dose response at fixed temperature), and dose response when irradiated at low temperatures.

Materials and Equipment:
A. Harwell alanine pellet dosimeters
B. Microfuge tubes
C. Polypropylene "snap-cap" tubes
D. Bruker EPR spectrometer (eScan) system
 1. Electronics Unit (Model E2043000, Serial No. 0133)
 2. Magnetic Unit (Model E2044000, Serial No. 0133)
 3. Pellet probe PH00019
E. Denver M-220 analytical (micro)balance (Ser. No. P112332)
F. NIST Gammacell 220 irradiator(GC207) and alanine pellet holder
G. NIST temperature controller and recorder
H. Dickson Temperature and Relative Humidity data logger (TP120, Ser. No. 02222169)

Experiment Details:

A. Sample Handling, Labeling and Storage

1. Individual dosimeters were stored in a polymer canister.
 b. Samples were provided to NIST for irradiation and stored (pre- and post-irradiation) in accordance with NIST's standard practices. Following irradiation:
 a. Individual pellets were identified with a sample number;
 b. Calibration samples were individually stored in microfuge tubes.
 c. Temperature samples were stored in polypropylene (snap-cap) tubes. All samples for a given dose and irradiation temperature were stored in a single tube.
2. Upon return from NIST, calibration and temperature dosimeters were identified according to
 d. Dosimeter manufacturer,
 e. Dosimeter batch,
 f. Nominal dose,
 g. Nominal irradiation temperature, and
 h. Dosimeter number (for replicate samples).

B. Irradiation Studies—Calibration and Temperature

1. Dosimeters were irradiated according to the irradiation schedule in Table 1
2. Calibration samples consisted of four (4) dosimeters at each dose point plus controls.
 b. Temperature samples consisted of six (6) dosimeters at each dose point plus controls.
1. All dosimeters to be used for the calibration and temperature studies were visually inspected. No samples needed to be replaced as a result of this inspection C. EPR Analysis of Dosimeters 1. Dosimeters were allowed to equilibrate to room conditions for a minimum of 24 hours following the end of irradiation before reading them.

2. The mass of each pellet was taken after EPR analysis was performed

3. To assess any change in dosimeter response with time, calibration and selected temperature samples were reanalyzed during subsequent sample analysis sessions for a period of at least one month following irradiation.

These dose ratios ranged from 0.984 to 1.018 (or −1.6% to +1.8%).

Temperature data and analysis for doses of 5, 25, 50, 60, 80 and 100 kGy. demonstrate high precision among replicate samples at each dose point. The highest % CV value, 1.88%, occurred at 100 kGy.

TABLE 1

Irradiation Schedule

| Nominal dose | Nominal Irradiation temperature (° C.) | | | | | | | | | | | | |
|---|---|---|---|---|---|---|---|---|---|---|---|---|---|
| (kGy, water) | −75 | −55 | −45 | −35 | −25 | −10 | 0 | 5 | 15 | 25* | 25 | 35 | 50 |
| 0.5 | X | X | X | X | X | X | X | X | X |   | X | X | X |
| 5 | X | X | X | X | X | X | X | X | X | X | X | X | X |
| 10 |   |   |   |   |   |   |   |   |   | X |   |   |   |
| 25 | X | X | X | X | X | X | X | X | X | X | X | X |   |
| 40 |   |   |   |   |   |   |   |   |   | X |   |   |   |
| 50 | X | X | X | X | X | X | X | X | X | X | X | X | X |
| 55 |   |   |   |   |   |   |   |   |   | X |   |   |   |
| 60 | X | X |   | X |   | X |   | X |   | X | X | X |   |
| 70 |   |   |   |   |   |   |   |   |   | X |   |   |   |
| 80 | X | X | X | X | X | X | X | X | X | X | X | X |   |
| 85 |   |   |   |   |   |   |   |   |   | X |   |   |   |
| 100 | X | X |   | X |   | X |   | X |   | X | X | X |   |
| 115 |   |   |   |   |   |   |   |   |   | X |   |   |   |
| 130 |   |   |   |   |   |   |   |   |   | X |   |   |   |

NOTE:
*denotes that samples irradiated (at this nominal temperature) using the NIST holder routinely used for performing calibration of dosimeters of this type. All other samples irradiated using NIST's special temperature holder.

Results and Data Analysis

Figure 4:
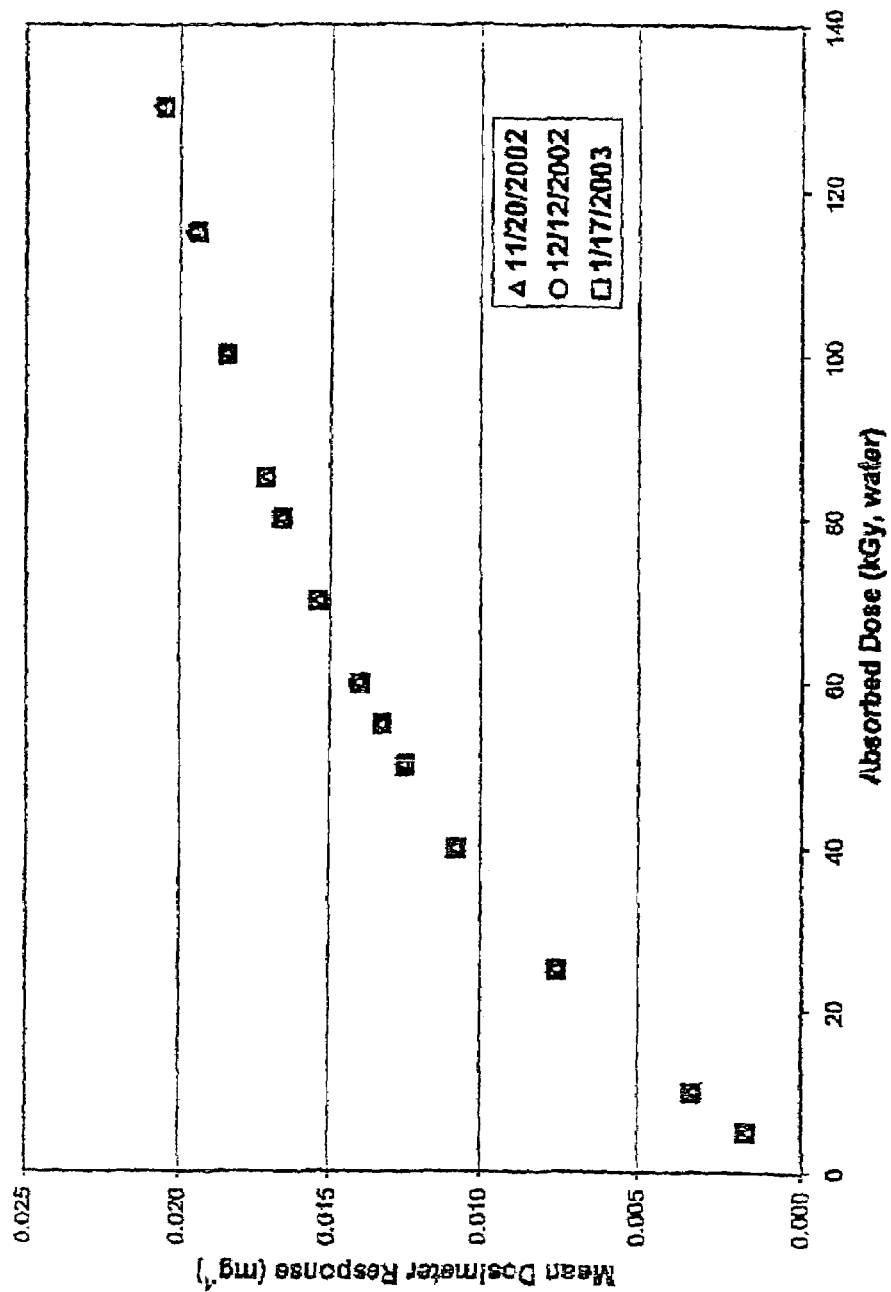
FIG. 4 shows the comparability of average measurements for alanine dosimeters irradiated with gamma irradiation taken over time.

Calibration data for EPR measurements showed high precision among replicate samples at each dose point. The highest % CV value, 0.55%, was at 85 kGy. This same trend occurred when these same dosimeters were read again about one or two months later. FIG. 4 illustrates the comparability of average (mean) measurements over a 3-month period for dosimeters irradiated at various temperatures to various total doses. Sample masses were consistent with the manufacturer's batch mass distribution range (59.5 to 61.2 mg).

Irradiation temperature varied for each group of dosimeter samples, ranging from 22.6 to 26.2° C., with an average of 24.4±1.1° C. By convention, 25° C. was used as the calibration reference temperature.

Figure 5:
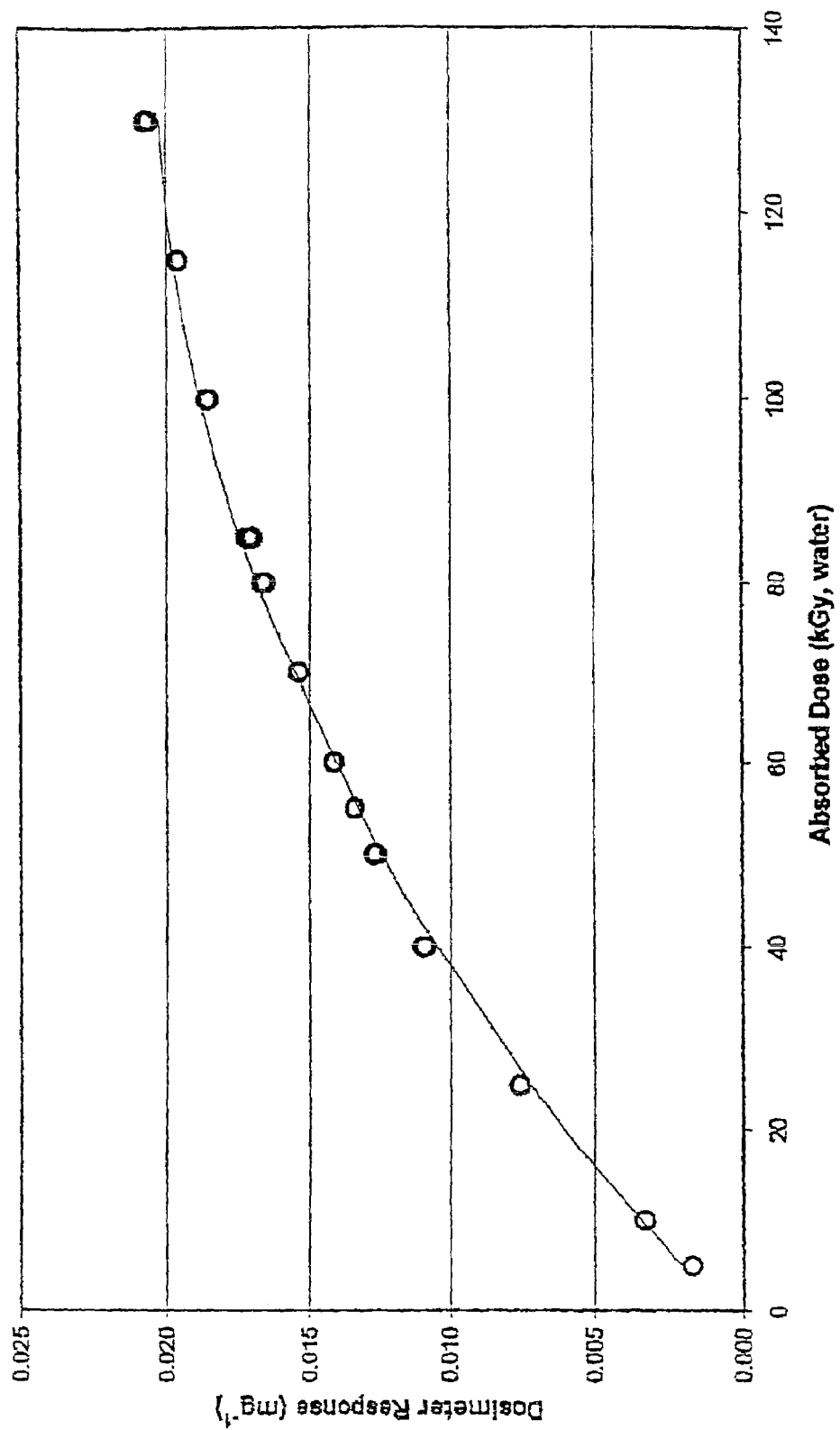
FIG. 5 shows a plot of mass-corrected dosimeter response versus absorbed dose over a calibration range for alanine dosimeters irradiated with gamma irradiation to various total doses.

FIG. 5 is a plot of the mass-corrected dosimeter response (Ratio/mg) vs. absorbed dose over the dynamic calibration range for alanine dosimeters irradiated with gamma irradiation. FIG. 5 illustrates a non-linear relationship.

Inverting the axes, we developed a mathematical function that describes the dose-response, D(R), relationship. A calibration curve (for fixed temperature T=25° C.) was developed covering the range 25 to 115 kGy. (See FIG. 6). The resulting equation is expressed as follows:

$$D(R)=22676188.37R^3-552494.84R^2+9102.47R-22.24$$

where

D=dose in kilograys (water), and

R=mass-corrected response at 25° C.

Coefficients have been rounded to 2 decimal places.

Figure 6:
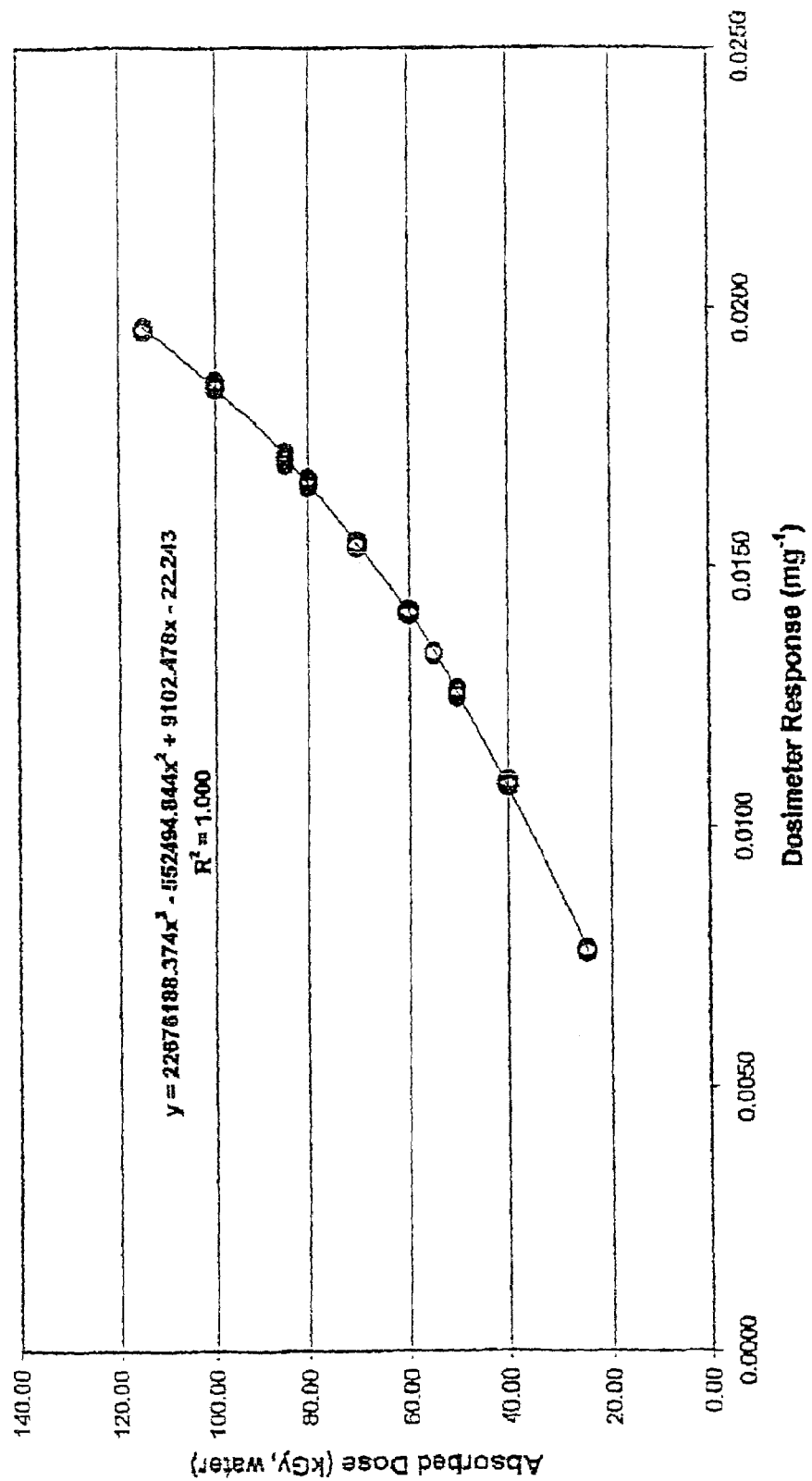
FIG. 6 shows a calibration curve (T=25° C.) for an alanine dosimeter irradiated with gamma irradiation to total doses of 25 to 115 kGy.

Besides observing a high $R^2$ value (indicating a high correlation between the variables), the suitability of the expression was assessed by substituting the mass-corrected dosimeter response into the analytical equation in FIG. 6.

Figure 7:
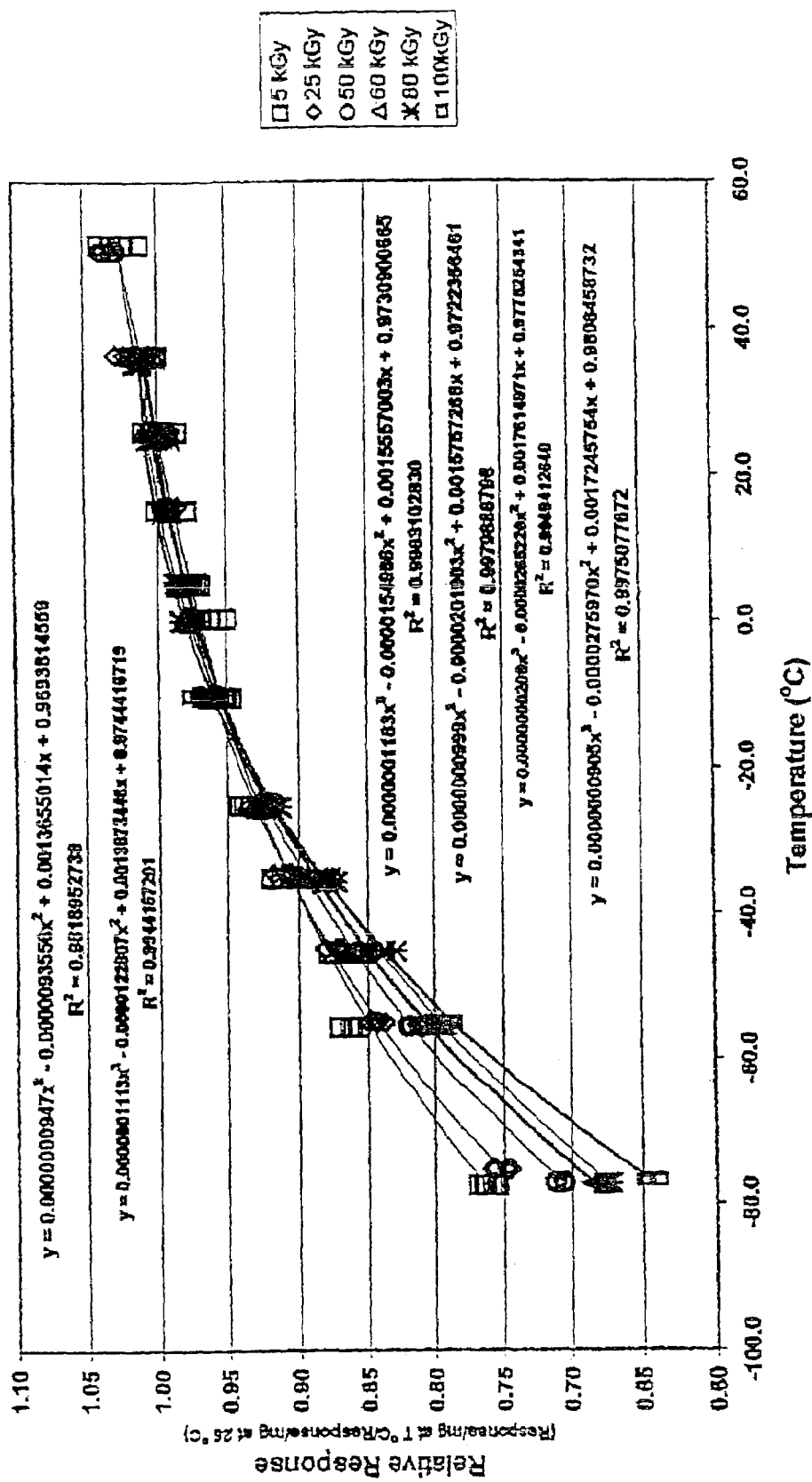
FIG. 7 shows a plot of relative response versus temperature for alanine dosimeters irradiated with gamma radiation between −77 and 50° C. to various total doses.

FIG. 7 is a plot of relative dosimeter response (relative to the mean dosimeter response at 25° C.) vs. irradiation temperature for each dose.

At dry ice temperatures, the dosimeter response (relative to 25° C.) decreases by approximately 23% to 25% for doses of 5 and 25 kGy, and by approximately 30% to 35% for doses of 50, 60, 80 and 100 kGy. At fixed dose, the dosimeter response as a function of irradiation temperature is predictable and can be described by a mathematical relationship. This mathematical relationship is dose-dependent, especially below approximately −10° C.

The suitability of each of the mathematical expressions shown in FIG. 7 was assessed by substituting the irradiation temperature into the analytical equation corresponding to the specified dose to obtain a predicted relative response. The predicted relative response was compared to the actual relative response by dividing one quantity by the other. Limiting the assessment to two representative expressions, the ratio at 50 kGy ranged from 0.986 to 1.013 (or −1.4% to +1.3%), and the ratio at 60 kGy ranged from 0.987 to 1.011 (or −1.3% to +1.1%).

To determine doses in the range 25–115 kGy and for irradiation temperatures (T) covering the range of −78 to +50° C., the measured response $(R_M)_{T° C.}$ was first divided by a temperature correction factor relative to 25° C. $(CF)_{25° C.}$:

$$R_{25° C.}=(R_M)T° C./(CF)_{25° C.}:$$

and then the dose response equation, D(R), was applied.

To test this approach, we determined the temperature-corrected response, $R_{25° C.}$, for the 50 kGy temperature data, and then computed the dose using the dose response equations, supra.

The predicted dose was compared to the experimentally determined dose by dividing one quantity by the other to get a ratio of doses. The dose ratio at 50 kGy over the temperature range ranged from 0.976 to 1.014 (or −2.6% to +1.4%).

Figure 8:
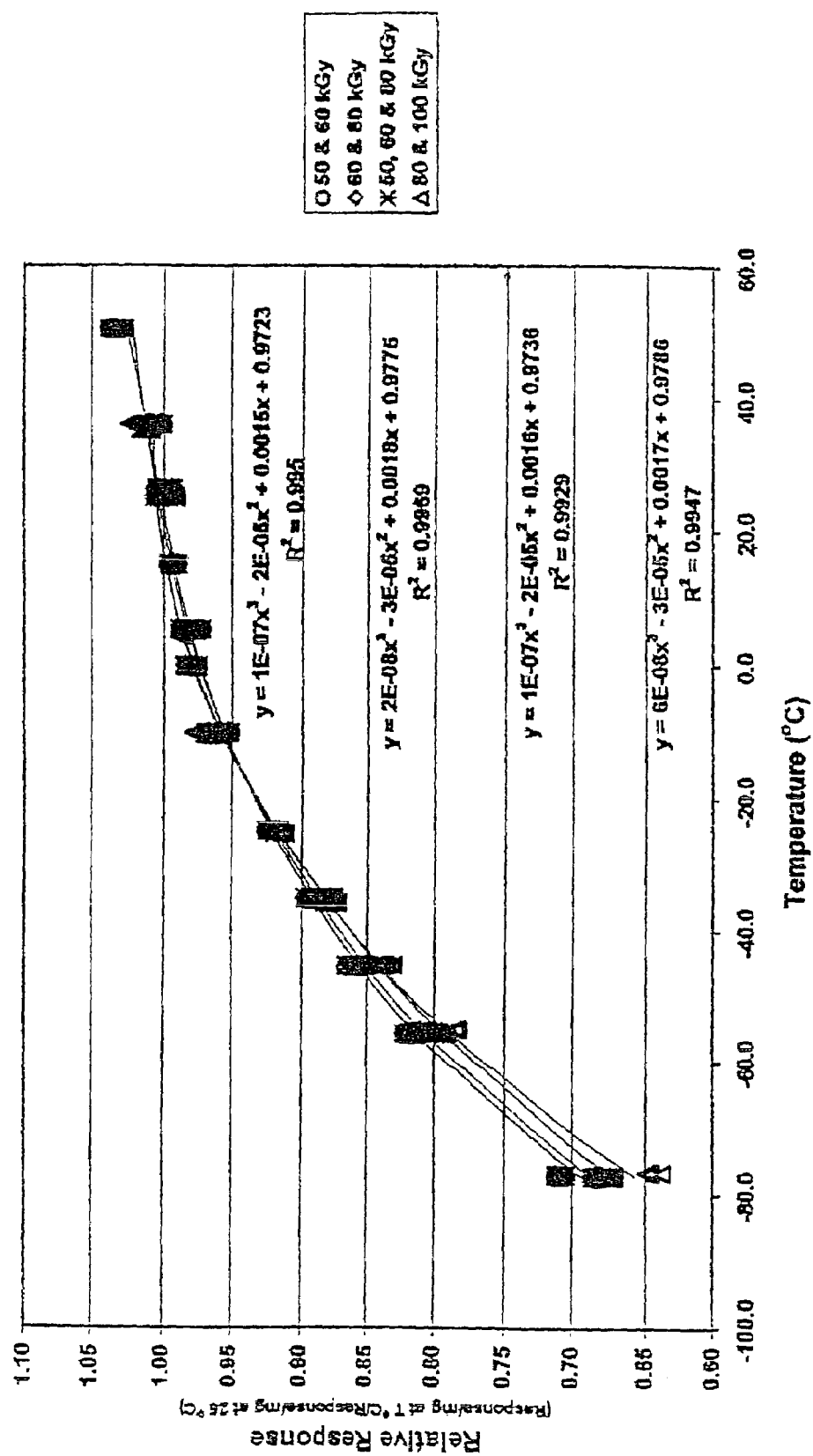
FIG. 8 shows a plot or relative response versus temperature for alanine dosimeters irradiated with gamma irradiation between −77 and 50° C. to various total doses.

As noted above, the CF value is dose-dependent. Practically, it is preferable to develop a single temperature correction (function) that covers as broad a dose range as possible. To assess the ability to accurately predict the dose using dose range-based CF values, calibration data were combined into dose ranges—50 & 60 kGy; 50, 60 & 80 kGy; 60 & 80 kGy; and 80 & 100 kGy—and plotted (see FIG. 8).

Figure 9:
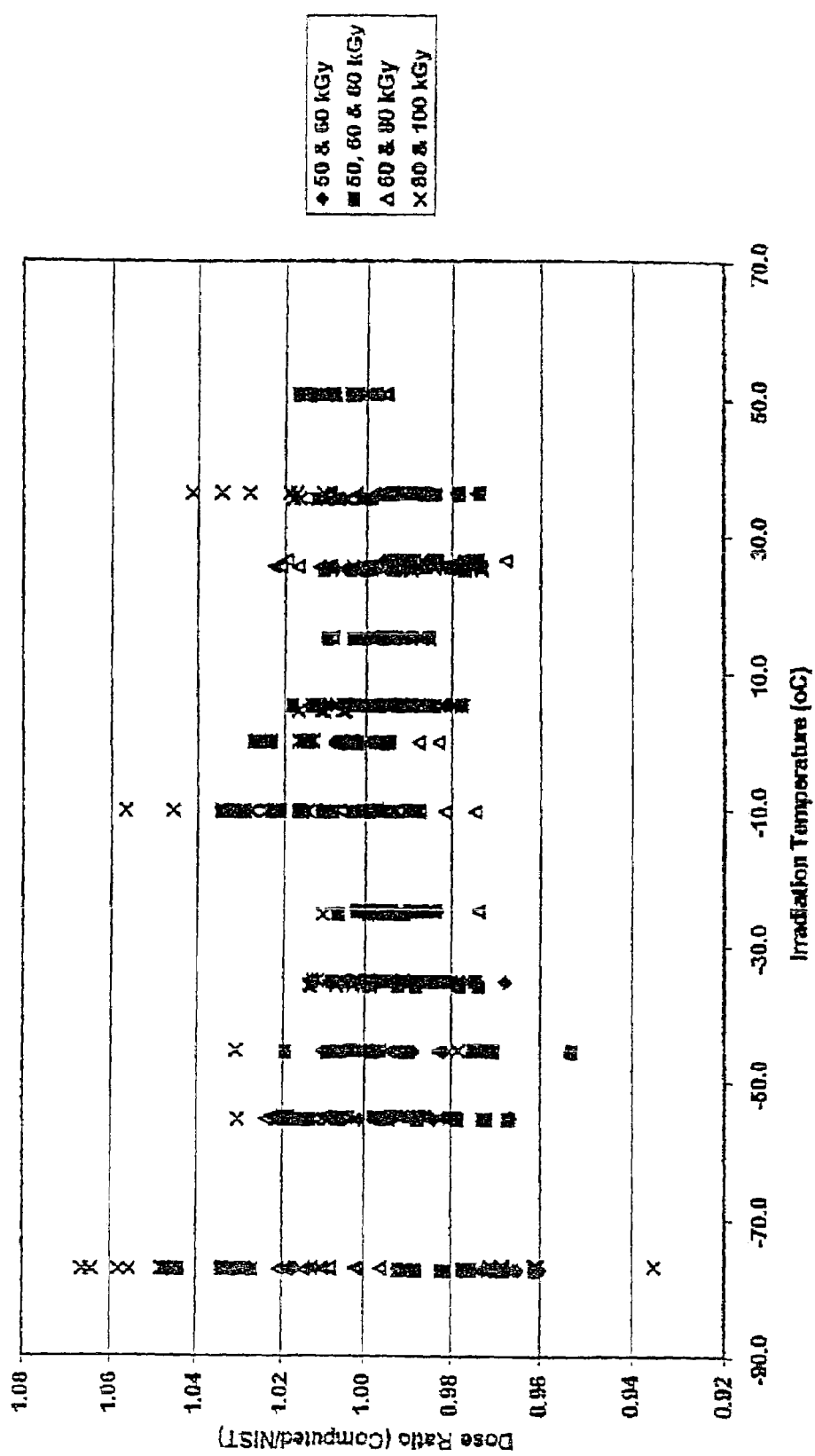
FIG. 9 shows the comparison of computed dose to reported dose for alanine dosimeters irradiated with gamma irradiation between −77 and 50° C. to various total doses.

The resulting equations were used to compute the $R_{25°\ C.}$ and the absorbed dose using the calibration curve above. FIG. 9 illustrates the comparison of computed dose to the reported dose (for each of the four dose ranges) as a function of irradiation temperature.

a. 50 and 60 kGy and T=−78 to +50° C.:

$$CF=0.000000133T^3-0.000016354T^2+0.001539890T+0.972303706$$

| Dose ratios | |
|---|---|
| Minimum: | 0.96 |
| Maximum: | 1.03 |
| Mean ± SD: | 0.993 ± 0.013 | b. 60 and 80 kGy and T=−78 to +35° C.:

$$CF=0.0000000427T^3-0.0000243867T^2+0.0017031262T+0.9757045570$$

| Dose ratios | |
|---|---|
| Minimum: | 0.97 |
| Maximum: | 1.03 |
| Mean +/− SD: | 1.001 ± 0.013 | c. 50, 60 and 80 kGy and T=−78 to +50° C.:

$$CF=0.000000104T^3-0.000018740T^2+0.001637463T+0.973579951$$

| Dose ratios | |
|---|---|
| Minimum: | 0.95 |
| Maximum: | 1.05 |
| Mean +/− SD: | 0.997 ± 0.017 | d. 80 and 100 kGy and T=−78 to +35° C.:

$$CF=0.0000000611T^3-0.0000265639T^2+0.0017373535T+0.9786412509$$

| Dose ratios | |
|---|---|
| Minimum: | 0.94 |
| Maximum: | 1.06 |
| Mean +/− SD: | 1.007 ± 0.022 |

Considering the broadest dose range, 50 to 80 kGy, computed and experimentally obtained doses agreed generally to within about 3%.

Figure 10:
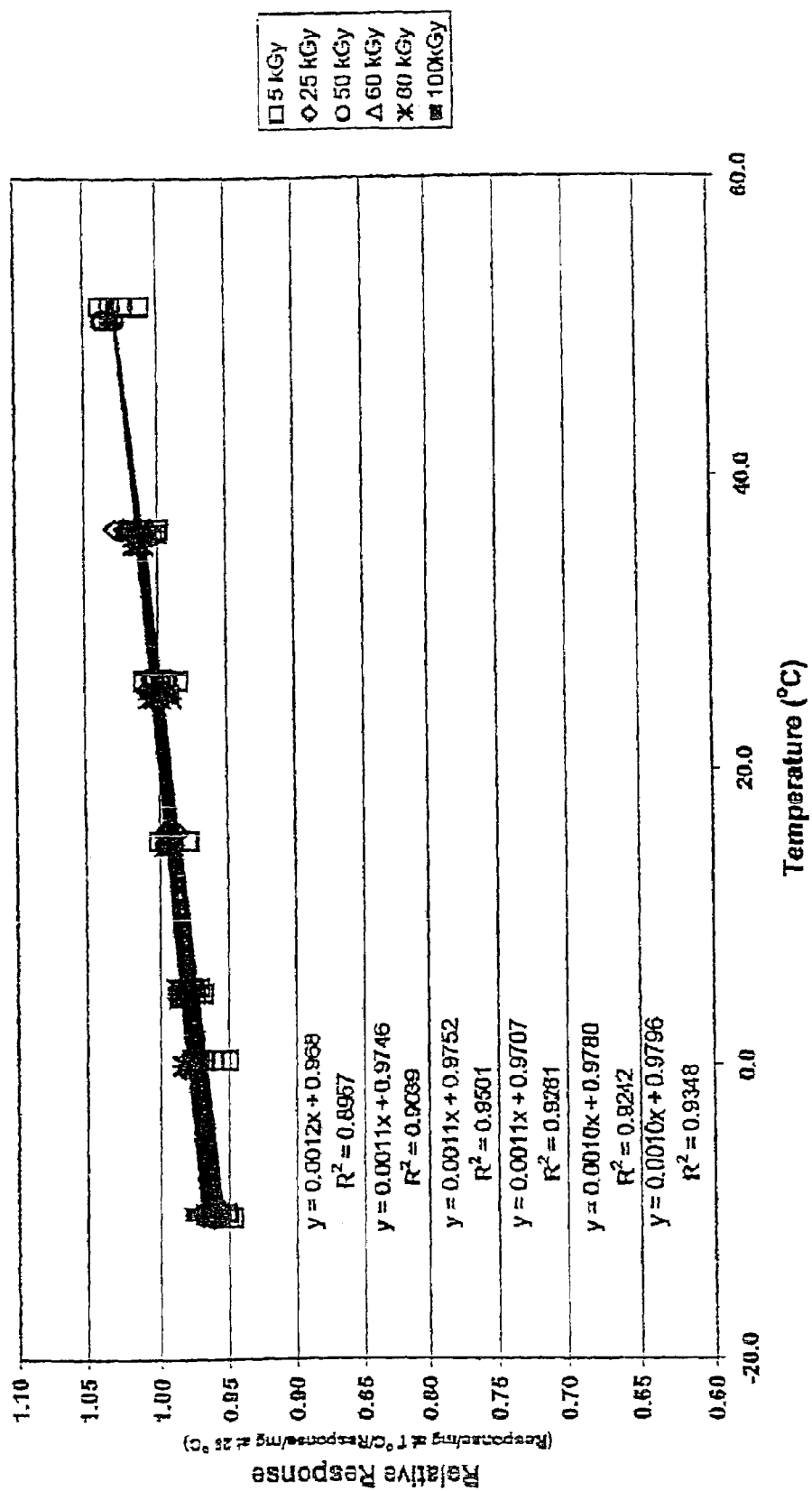
FIG. 10 shows response as a function of temperature for alanine dosimeters irradiated with gamma irradiation between −10 and 50° C. to various total doses.

As noted above, the temperature response appears to be dose independent above approximately −10° C. This is illustrated in FIG. 10 where the response as a function of temperature increases linearly, having a slope ~+0.0011, or +0.11%/° C. over the dose range of 5 to 100 kGy. Thus, over the range of −10 to +50° C., a scalar temperature correction factor can be applied that does not depend on the dose.

Figure 11:
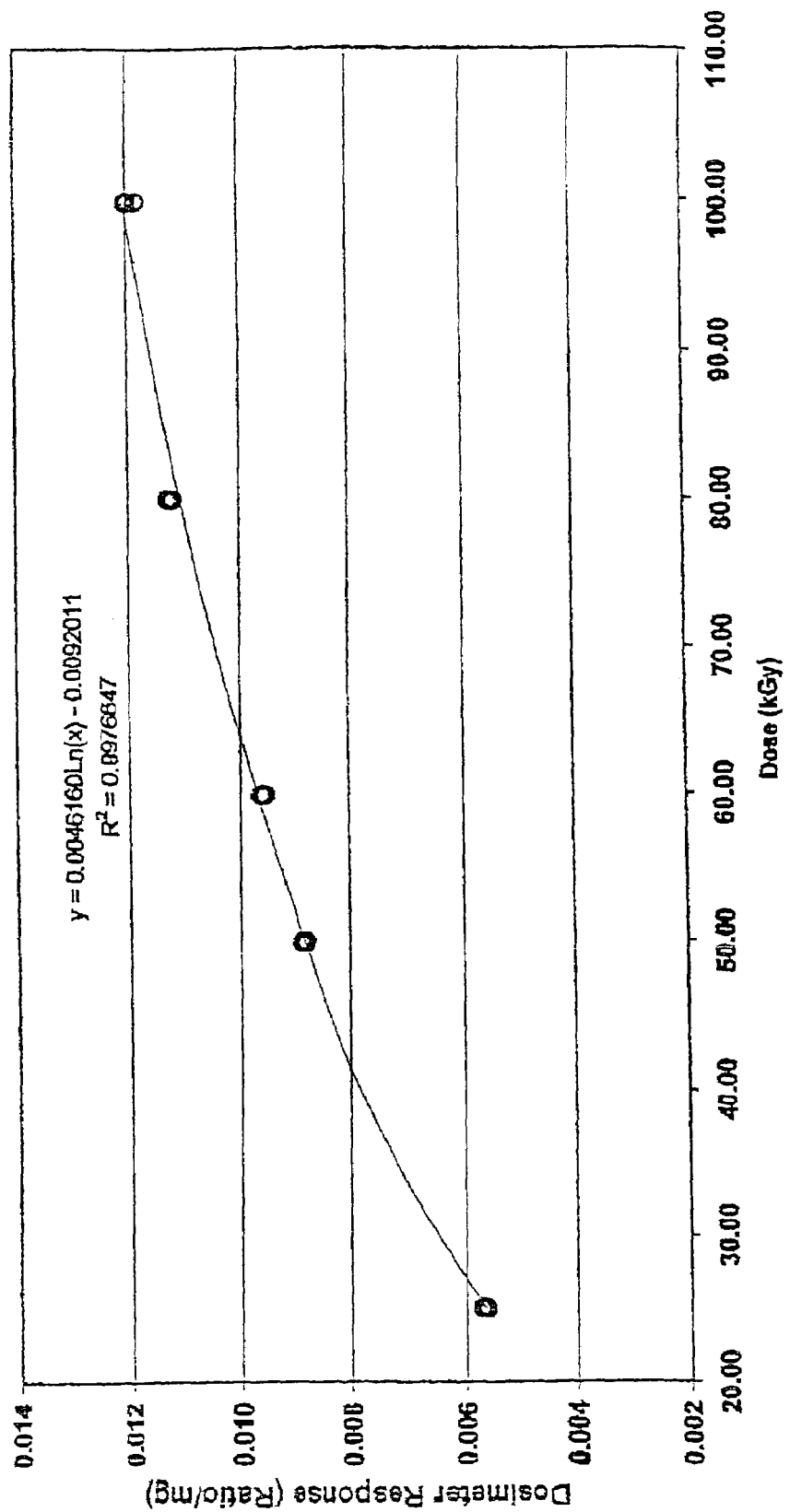
FIG. 11 shows a scatter plot (response versus dose) at dry ice temperature over the dose range of 25 to 100 kGy.

FIG. 11 shows a scatter plot (response vs. dose) at dry ice temperature (−77.4 to −75.4° C.) over the dose range of 25 to 100 kGy. The logarithmic equation, Response=0.00461601n (Dose)−0.0092011, can easily be translated to develop a dose(D)-response(R) relationship as follows:

$$D(R)=e^{((R+0.0092011)/0.0046160)}$$

Using this equation to compute the dose, and conducting a similar analysis of the computed (fitted) and reported (actual) doses, the following was observed regarding the dose ratios:

| Dose ratios | |
|---|---|
| Minimum: | 0.95 |
| Maximum: | 1.05 |
| Mean +/− SD: | 1.000 ± 0.023 |

The average dose ratios for each dose level ranged from 0.98 to 1.02 (i.e. agreement within 2%) with the exception of 80 kGy data, where ratio was 1.037. Thus, doses computed using this low-temperature calibration curve provides agreement with reported doses to within 4%.

Conclusions

These dosimeters may be used for measuring absorbed doses as shown below:

Based upon calibration data in the range of 25–115 kGy, dose (D) at fixed temperature (T=25° C.) within this range can be accurately predicted using the following mathematical expression:

$$D(kGy,\ water)_{25°\ C.}=22676188.3743057R_{25°\ C.}^3-552494.8437186R_{25°\ C.}^2+9102.4775300R_{25°\ C.}-22.2431768$$

where $R_{25°\ C.}$=mass-corrected response (mg$^{-1}$) for irradiation temperature(T)=25° C.

Alternately, if temperature during irradiation is controlled to maintain dry ice temperature (−77.4 to −75.4° C.), the following mathematical expression can be used:

$$D(kGy,\ water)_{25°\ C.}=e^{((R+00092011)/0.0046160)}$$

where R=mass-corrected response (mg$^{-1}$) for irradiation temperature(T)=−78° C.

At fixed dose, the dosimeter response as a function of irradiation temperature is predictable and can be described by a mathematical relationship. This relationship appears linear for temperatures above −10° C. and becomes non-linear for temperatures below approximately −10° C. Considering the entire temperature range, this mathematical relationship is dose-dependent. However, above ~−10° C. the relationship appears dose-independent, having a correction factor of approximately +1.1%/° C.

Perform the following generalized steps to determine absorbed doses based on irradiation temperatures in the range of −78 to +50° C. Correct the measured response $(R_M)_{T°\ C.}$ to its corresponding value at the reference temperature of +25° C. ($R_{25°\ C.}$) using the appropriate temperature correction factor (CF):

$$R_{25°\ C.}=(R_M)_{T°\ C.}/CF$$

i. For irradiation temperature (T) below −10° C. and dose range 50–80 kGy, $$CF=0.000000104T^3-0.000018740T^2+0.001637463T+0.973579951$$

ii. For irradiation temperature (T) below −10° C. and dose range above 80 kGy and less than 90 kGy, $$CF=0.0000000209T^3-0.0000265220T^2+0.0017614971T+0.9775254341$$

iii. For irradiation temperature (T) below −10° C. and dose range above 90 kGy and less than 100 kGy, $$CF=0.0000000905T^3-0.0000275970T^2+0.0017245754T+0.9808458732$$

iv. For irradiation temperature (T) equal to or above −10° C. (dose-independent), $$CF=1+[(T-25)(0.0011)]$$

Having now fully described this invention, it will be understood to those of ordinary skill in the art that the methods of the present invention can be carried out with a wide and equivalent range of conditions, formulations and other parameters without departing from the scope of the invention or any embodiments thereof.

All patents and publications cited herein are hereby fully incorporated by reference in their entirety. The citation of any publication is for its disclosure prior to the filing date and should not be construed as an admission that such publication is prior art or that the present invention is not entitled to antedate such publication by virtue of prior invention.

What is claimed is:

1. A device for measuring the amount of energy absorbed by a product undergoing sterilization with radiation, comprising:
    (i) an effective amount of at least one material that absorbs radiation in a quantifiable manner; and
    (ii) an effective amount of at least one cooling agent for maintaining said at least one material within a predetermined temperature range between −120° C. and ambient temperature during irradiation.

2. The device according to claim 1, wherein said at least one material that absorbs radiation is selected from the group consisting of alanine, cellulose acetate, ethanol-chlorobenzene and radiochromic films.

3. The device according to claim 1, wherein said at least one cooling agent comprises dry ice.

4. The device according to claim 1, wherein said at least one cooling agent is of sufficient volume to contain at least a portion of said at least one material that absorbs radiation.

5. The device according to claim 1, wherein said at least one cooling agent is in the form of particles.

6. The device according to claim 5, wherein said particles have an average volume of not more than 17 cm$^3$.

7. The device according to claim 1, wherein said particles have an average volume of not more than 1 cm$^3$.

8. The device according to claim 1, wherein said at least one cooling agent is in the form of a solid or semi-solid.

9. The device according to claim 1, further comprising a container of sufficient volume to contain at least a portion of said cooling agent and at least a portion of said material.

10. The device according to claim 9, wherein said container is a vacuum Dewar.

11. The device according to claim 1, wherein each endpoint of said temperature range is less than the freezing point of said product.

12. The device according to claim 1, wherein each endpoint of said temperature range is less than −20° C.

13. The device according to claim 1, wherein each endpoint of said temperature range is less than −40° C.

14. The device according to claim 1, wherein each endpoint of said temperature range is less than −60° C.

15. The device according to claim 1, wherein each endpoint of said temperature range is less than −70° C.

16. A method for determining the amount of energy absorbed by a product undergoing irradiation, comprising:
    (a) placing within a suitable container at least one product to be sterilized and at least one device comprising:
        (i) at least one material that absorbs radiation in a quantifiable manner; and
        (ii) an effective amount of at least one cooling agent for maintaining said material within a predetermined temperature range between 120° C. and ambient temperature during irradiation;
    (b) irradiating with gamma radiation said container containing said at least one product and said at least one device; and
    (c) analyzing said at least one material to determine the amount of energy absorbed during said irradiation.

17. A method for maintaining the temperature of a product undergoing irradiation within a predetermined temperature range between −120° C. and ambient temperature, comprising:
    (a) placing at least one product to be irradiated comprising at least one material that absorbs radiation in a quantifiable manner in a suitable container having at least one side and a bottom, wherein the volume defined by said container is greater than the volume of said at least one product;
    (b) placing an effective amount of at least one cooling agent in said container between said at least one product and said at least one side; and
    (c) irradiating with gamma radiation said container containing said at least one product and said at least one cooling agent.

18. The method according to claim 16 or 17, wherein said at least one product further comprises a biological material.

19. The method according to claim 18, wherein said biological material is selected from the group consisting of dextrose, antithrombin III, plasma, plasminogen, urokinase, thrombin, trypsin, purified protein fraction, blood, blood cells, alpha-1 proteinase inhibitor, digestive enzymes, blood proteins and tissue.

20. The method according to claim 19, wherein said tissue is selected from the group consisting of heart valves, ligaments and dimineralized bone matrix.

21. The method according to claim 19, wherein said digestive enzymes are selected from the group consisting of galactosidases and sulfatases.

22. The method according to claim 19, wherein said blood proteins are selected from the group consisting of albumin, Factor VIII, Factor VII, Factor IV, fibrinogen, monoclonal immunoglobulins and polyclonal immunoglobulins.

23. The method according to claim 19, wherein said tissue is selected from the group consisting of tendons, nerves, bone, teeth, bone marrow, skin grafts, cartilage, corneas, arteries, veins and organs for transplantation.

24. The method according to claim 18, further comprising at least one stabilizer in an amount effective to protect said biological material from said irradiation.

25. The method according to claim 24, wherein said at least one stabilizer is selected from the group consisting of DMSO, mannitol, ascorbic acid and salts and esters thereof, trehalose and propylene glycol.

26. The method according to claim 16 or 17, wherein said at least one cooling agent comprises dry ice.

27. The method according to claim 16 or 17, wherein said at least one cooling agent is in the form of particles.

28. The method according to claim 27, wherein said particles have an average volume of not more than 17 cm$^3$.

29. The method according to claim 28, wherein said particles have an average volume of not more than 1 cm$^3$.

30. The method according to claim 16 or 17, wherein said at least one cooling agent is in the form of a solid or semi-solid.

31. The method according to claim 16 or 17, wherein said container is a vacuum Dewar.

32. The method according to claim 16 or 17, wherein said container has a front side and a back side and a first side and a second side.

33. The method according to claim 32, wherein said container is a foam box.

34. The method according to claim 32, wherein said at least one cooling agent is placed between said at least one product and said first side, between said at least one product and said second side, or a combination thereof.

35. The method according to claim 16 or 17, wherein said at least one material is selected from the group consisting of alanine, cellulose acetate, ethanol-chlorobenzene and radiochromic films.

36. The method according to claim 16 or 17, wherein said at least one product is frozen.

37. The method according to claim 16 or 17, wherein each endpoint of said temperature range is less than ambient temperature.

38. The method according to claim 16 or 17, wherein each endpoint of said temperature range is less than the freezing point of said at least one product.

39. The method according to claim 16 or 17, wherein each endpoint of said temperature range is less than −70° C.

40. The method according to claim 16 or 17, wherein each endpoint of said temperature range is less than the glass transition point of said at least one product.

41. The method according to claim 16 or 17, wherein said temperature range is less than 10° C.

42. The method according to claim 16 or 17, wherein said temperature range is less than 2° C.

43. The method according to claim 16 or 17, wherein said temperature range is less than 0.1° C.

44. The method according to claim 16 or 17, wherein said temperature range is less than 0.1° C. per kGy of radiation.

45. The method according to claim 16 or 17, wherein said temperature range is less than 0.02° C. per kGy of radiation.

* * * * *